US008106372B2

(12) United States Patent
Powers

(10) Patent No.: US 8,106,372 B2
(45) Date of Patent: Jan. 31, 2012

(54) QUICK RELEASE CONTAINMENT AND SHIELDING APPARATUS

(76) Inventor: Donald L. Powers, Oakdale, TN (US)

( * ) Notice: Subject to any disclaimer, the term of this patent is extended or adjusted under 35 U.S.C. 154(b) by 124 days.

(21) Appl. No.: 12/506,584

(22) Filed: Jul. 21, 2009

(65) Prior Publication Data

US 2009/0278061 A1 Nov. 12, 2009

Related U.S. Application Data

(63) Continuation of application No. 12/352,218, filed on Jan. 12, 2009, now abandoned, which is a continuation of application No. 10/947,681, filed on Sep. 23, 2004, now Pat. No. 7,537,560.

(60) Provisional application No. 60/507,311, filed on Sep. 30, 2003.

(51) Int. Cl.
*G21F 5/00* (2006.01)
*A61N 5/00* (2006.01)

(52) U.S. Cl. ........................ 250/507.1; 250/506.1; 600/5
(58) Field of Classification Search ..... 250/505.1–507.1
See application file for complete search history.

(56) References Cited

U.S. PATENT DOCUMENTS

| | | | | |
|---|---|---|---|---|
| 4,081,688 | A * | 3/1978 | Fries | 250/506.1 |
| 4,673,813 | A * | 6/1987 | Sanchez | 250/506.1 |
| 5,672,883 | A * | 9/1997 | Reich | 250/507.1 |
| 5,991,136 | A * | 11/1999 | Kaczmarek et al. | 361/93.8 |
| 7,537,560 | B2 * | 5/2009 | Powers et al. | 600/5 |
| 2002/0145007 | A1 * | 10/2002 | Sawhney et al. | 222/137 |
| 2003/0222228 | A1 * | 12/2003 | Chen Fu et al. | 250/507.1 |

* cited by examiner

*Primary Examiner* — Jack Berman
*Assistant Examiner* — David E Smith
(74) *Attorney, Agent, or Firm* — Luedeka, Neely & Graham, P.C.

(57) ABSTRACT

A containment medical apparatus for use in association with medical treatments requiring radioactive substances has a tubular housing with a cap configured for closing an open end of the tubular housing. A quick release mechanism holds the cap on an open end of the tubular housing.

12 Claims, 28 Drawing Sheets

QUICK RELEASE CONTAINMENT AND SHIELDING APPARATUS

CROSS-REFERENCE(S) TO RELATED APPLICATION(S)

This is a continuation application of co-pending U.S. application Ser. No. 12/352,218 filed Jan. 12, 2009, entitled CONTAINMENT, SHIELDING, INFORMATION DISPLAY, DISTRIBUTION AND ADMINISTRATION OF RADIOACTIVE PHARMACEUTICALS which claims priority benefit to U.S. application Ser. No. 10/947,681 filed Sep. 23, 2004, entitled CONTAINMENT, SHIELDING, INFORMATION DISPLAY, DISTRIBUTION AND ADMINISTRATION OF RADIOACTIVE PHARMACEUTICALS, which claims priority benefit to U.S. Provisional Application Ser. No. 60/507,311 filed 30 Sep. 2003, and entitled CONTAINMENT, SHIELDING, INFORMATION DISPLAY, DISTRIBUTION AND ADMINISTRATION OF RADIOACTIVE PHARMACEUTICALS, all of which are incorporated herein by reference in their entireties.

FIELD

This disclosure relates to the field of containment devices. More particularly, this disclosure relates to containment and shielding devices for use with radiopharmaceuticals.

SUMMARY

In accordance with various embodiments of the present invention, a shielded containment medical apparatus is provided for housing and/or transporting medical treatments that include radioactive substances.

A first embodiment includes a containment apparatus for use in association with medical treatments that include radioactive substances, the apparatus including a tubular housing including a first end and a second end, a plurality of bores located proximate the first end of the tubular housing, and a plurality of movable objects located within the plurality of bores; a cap having a distal end and a proximal end, the proximal end including a receiver, wherein the proximal end is configured for interlocking with and covering the first end of the tubular housing; and a quick release mechanism. The quick release mechanism preferably includes a collar movably positioned proximate the first end of the tubular housing, the collar including a first end, a second end, and an engagement surface located proximate the first end of the collar. The quick release mechanism also preferably includes a biasing member engaged with the collar to bias the collar in a direction toward the first end of the tubular housing. The cap may be rapidly attached to the tubular housing by positioning the collar toward the second end of the tubular housing, placing the proximal end of the cap on the first end of the tubular housing, and moving the collar toward the first end of the tubular housing such that the plurality of movable objects are urged into the receiver as the engagement surface engages the plurality of movable objects and the plurality of movable objects engage with the receiver, thereby substantially interlocking the cap with the tubular housing, and wherein the cap may be rapidly removed from the tubular housing by moving the collar toward the second end of the tubular housing so that the engagement surface of the collar no longer urges the plurality of movable objects into the receiver, thereby substantially freeing the cap from the tubular housing.

Preferably, the containment apparatus includes a lower radioactive shield located within the tubular housing and an upper radioactive shield located within the quick release cap. Also, the engagement surface is preferably inclined.

The receiver preferably includes a groove located proximate the proximal end of the cap. Alternatively, the receiver includes a plurality of bores located proximate the proximal end of the cap.

The plurality of movable members may, for example, include a plurality of springs engaged with a plurality of pins for biasing the plurality of pins. Alternatively, the plurality of movable members further includes a plurality of balls located within the plurality of bores.

Another embodiment includes a containment apparatus for use in association with medical treatments that include radioactive substances wherein the apparatus includes a tubular housing including a first end and a second end; a cap having a distal end and a proximal end, the proximal end including a receiver, wherein the proximal end is configured for interlocking with and covering the first end of the tubular housing; and a quick release mechanism including a keyed rail including a key, the keyed rail extending from and attached to the proximal end of the cap; wherein the cap further includes a rail cavity, and wherein the housing further includes a slotted cavity including a slot along the length of the slotted cavity, and a cutout proximate the open end of the housing; and an opening located along the open end of the housing including a guide bearing located in the opening, wherein the keyed rail is slidably located on the guide bearing along the slotted cavity of the housing, and wherein the key may be mated with the slot in the cavity, thereby allowing the cap to be moved away from the housing while preventing the cap from rotating about the rail.

Yet another embodiment includes a containment apparatus for use in association with medical treatments that include radioactive substances, the apparatus including a tubular housing including a first end, a second end, and a plurality of extensions; a cap having a distal end, a proximal end, and a plurality of substantially planar surfaces; and a quick release mechanism including a flip top arm attached to at least two of the planar surfaces, the flip top arm including a pair of slots, each slot including an angled portion along an end of the slot closest to the cap, wherein at least two of the plurality of extensions are located within the slots, whereby the cap may be rapidly removed along a path defined by the movement of the flip top arm along the extensions.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Figure 1:
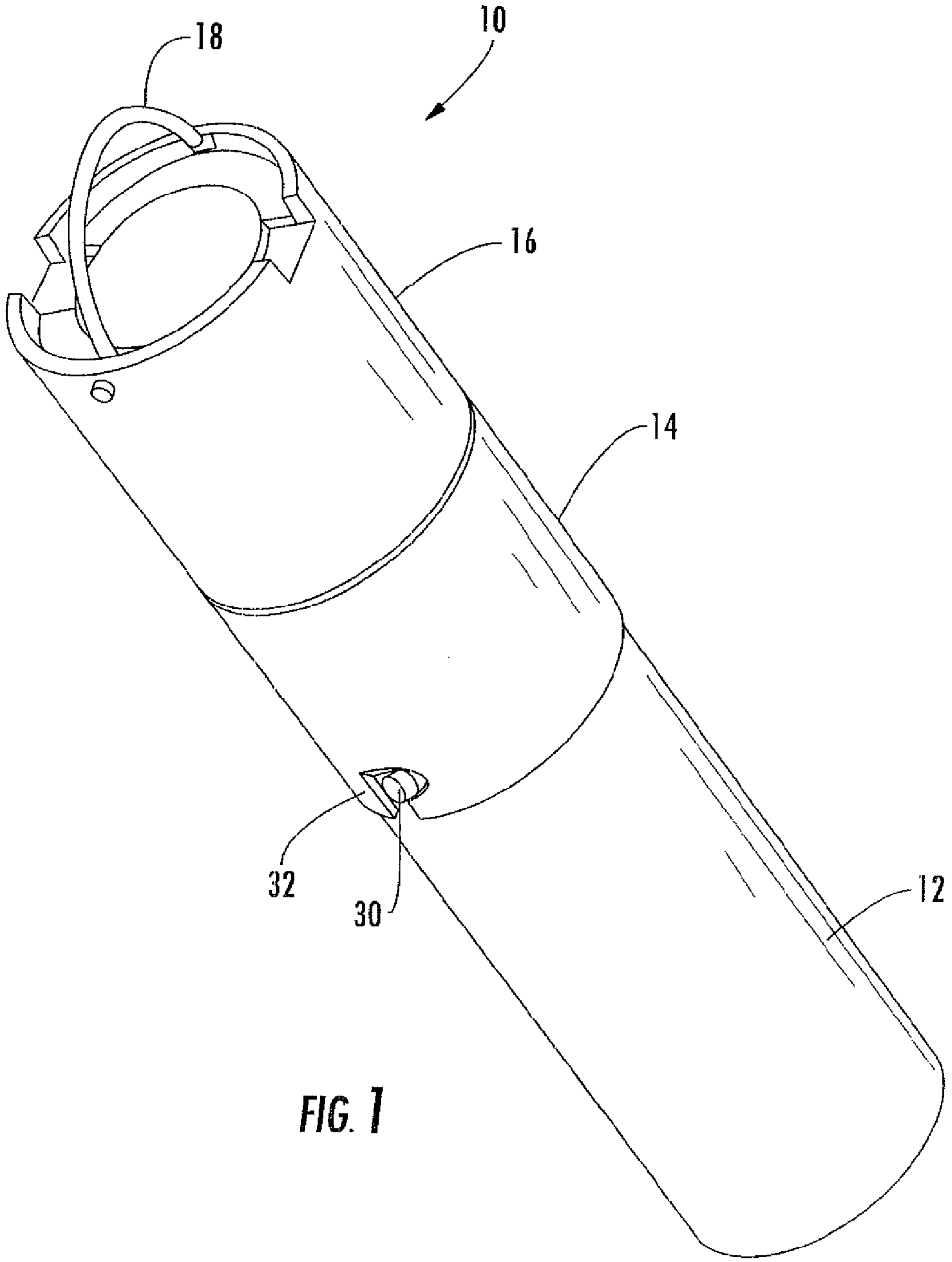
FIG. 1 is a view of the shielded radioactive medical container according to a preferred embodiment of the invention.

FIG. 1 illustrates a shielded radioactive medical container 10 for holding radioactive objects, most preferably a shielded syringe containing a radioactive solution, which allows a user to be exposed to a minimum amount of radiation. The shielded container 10 includes a housing 12, a quick release cap 16, a handle 18, and a collar 14. In a preferred embodiment, the container 10 is tubular to allow convenient handling and storage, and in a most preferred embodiment is cylindrical. A syringe, or other radioactive material, may be placed into the tubular housing for storage and transportation, and when the quick release cap 16 is secured in place, radiation will be contained and exposure measured at the external surface of the container 10 will be minimized. The container 10 is preferably dimensioned so that a single syringe will fit inside. However, the container 10 may be of any dimension, including dimensioned to fit all sized syringes, a plurality of syringes, or other objects.

Figure 2:
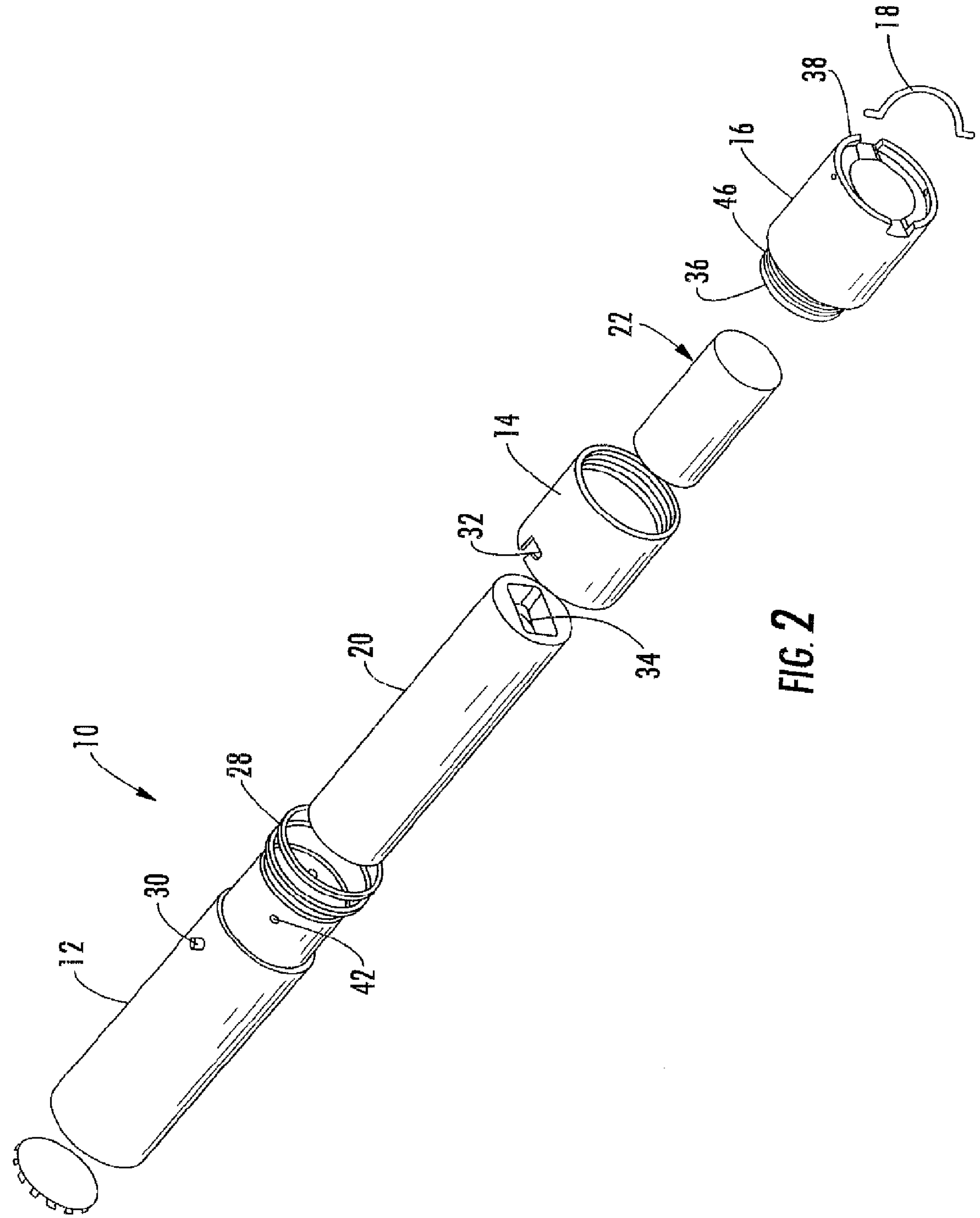
FIG. 2 is an exploded view of the shielded radioactive medical container according to a preferred embodiment of the invention.
Figure 5A:
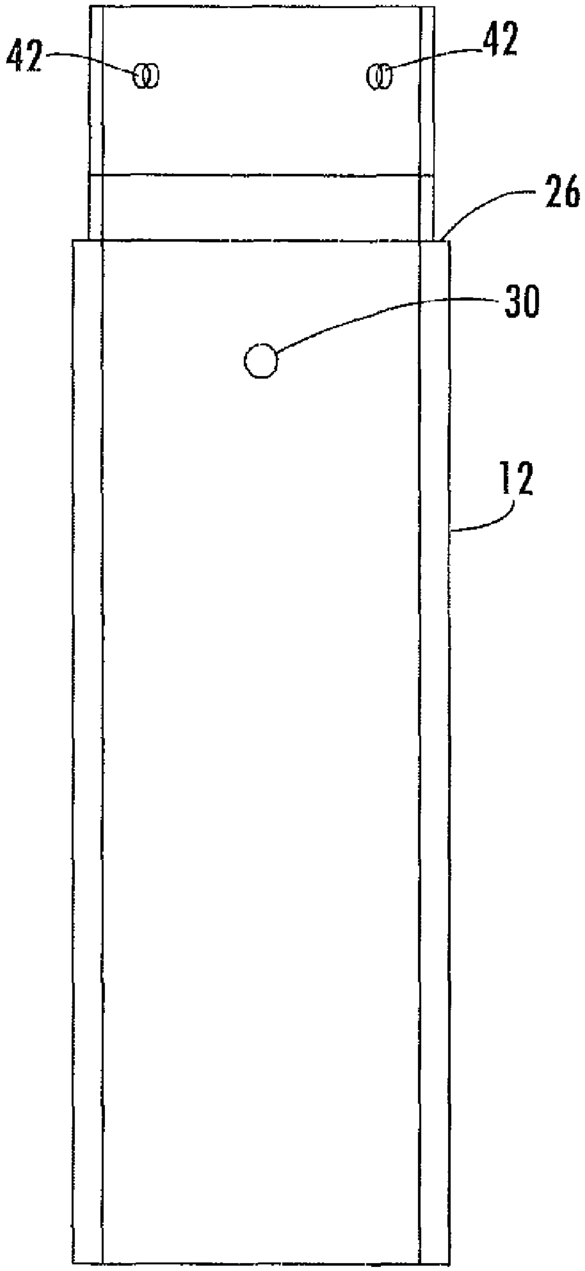
FIGS. 5*a-b* are views of the housing of the shielded radioactive medical container according to a preferred embodiment of the invention.
Figure 5B:
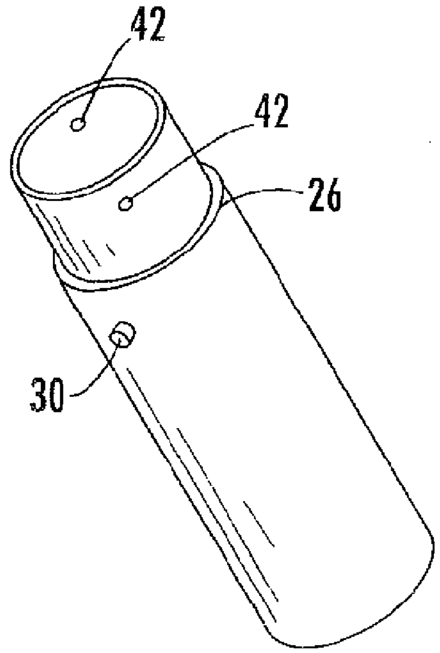
Figure 6A:
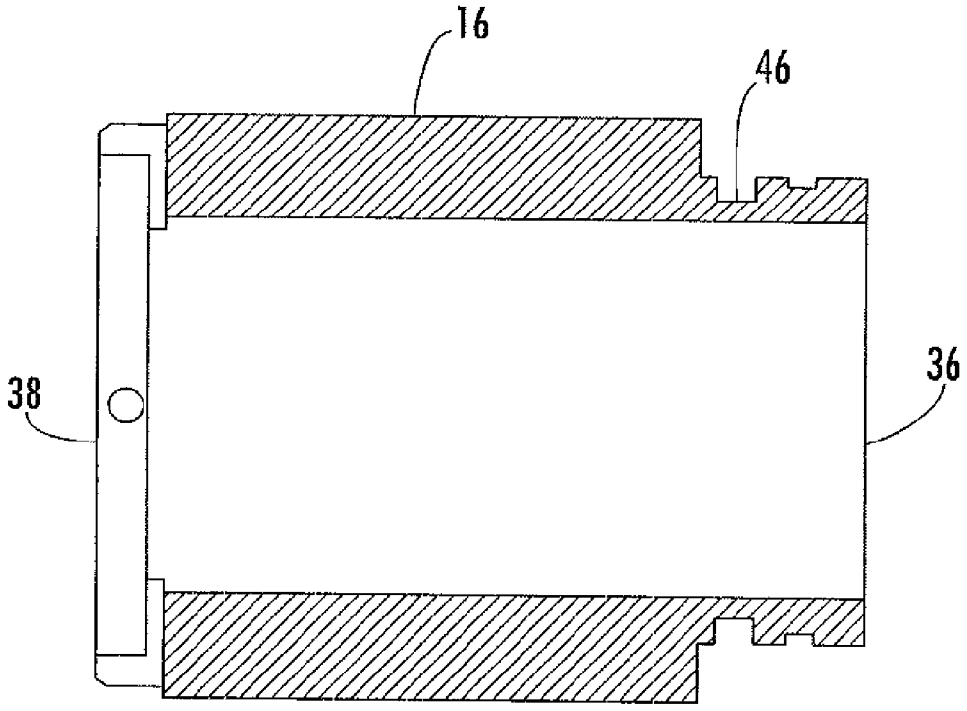
FIGS. 6*a-b* are views of the quick release cap of the shielded radioactive medical container according to a preferred embodiment of the invention.
Figure 6B:
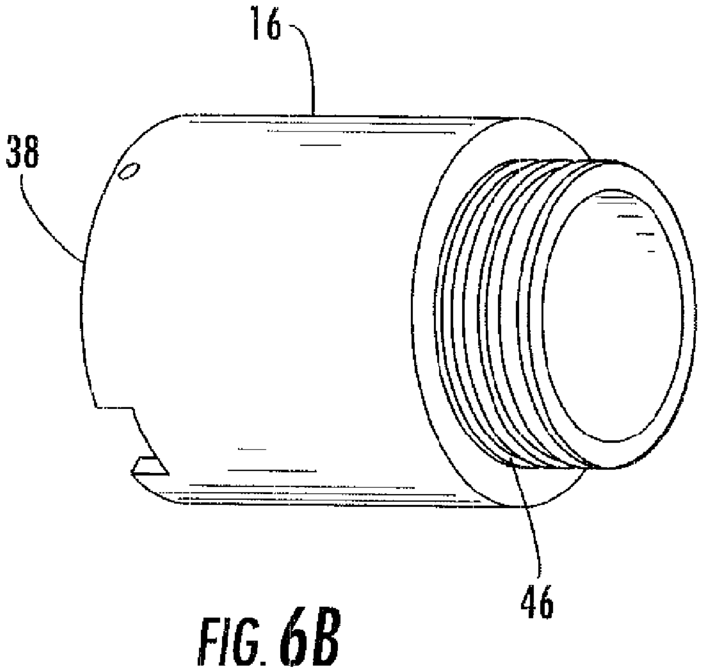

Referring now to FIG. 2, there is shown an exploded view of a preferred embodiment of the shielded radioactive medical container 10. As shown in FIGS. 5A and 5B, the housing 12 is tubular with an open end and a closed end. The tubular housing 12 is preferably cylindrical, but in alternate embodiments may be a square tube, rectangular tube or any other shaped tube.

Lower shield 20 is located in the interior of the housing 12 and preferably has a tubular configuration to fit snugly within the housing 12. The lower shield 20 has a cavity 34 with an opening which allows a radioactive object to be placed within the cavity 34 from the open end of the housing 12. The cavity 34 is preferably sized to allow a syringe to fit therein. The lower shield 20 may be made of any material which is suitable for shielding radiation, and is preferably lead or tungsten.

The open end of the housing 12 is configured so that the proximate end 36 of the quick release cap 16 fits inside of the housing 12. When the quick release cap 16 is secured onto the housing 12, the proximate end 36 of the cap 16 is located within the open end of the housing 12. An upper shield 22 is located within the interior of the quick release cap 16 and acts as a radioactive shield which closes off the cavity 34 in the lower shield 20 when the cap 16 is secured on the housing 12. The upper shield is preferably cylindrical in shape and made of the same material as the lower shield 20.

Figure 3:
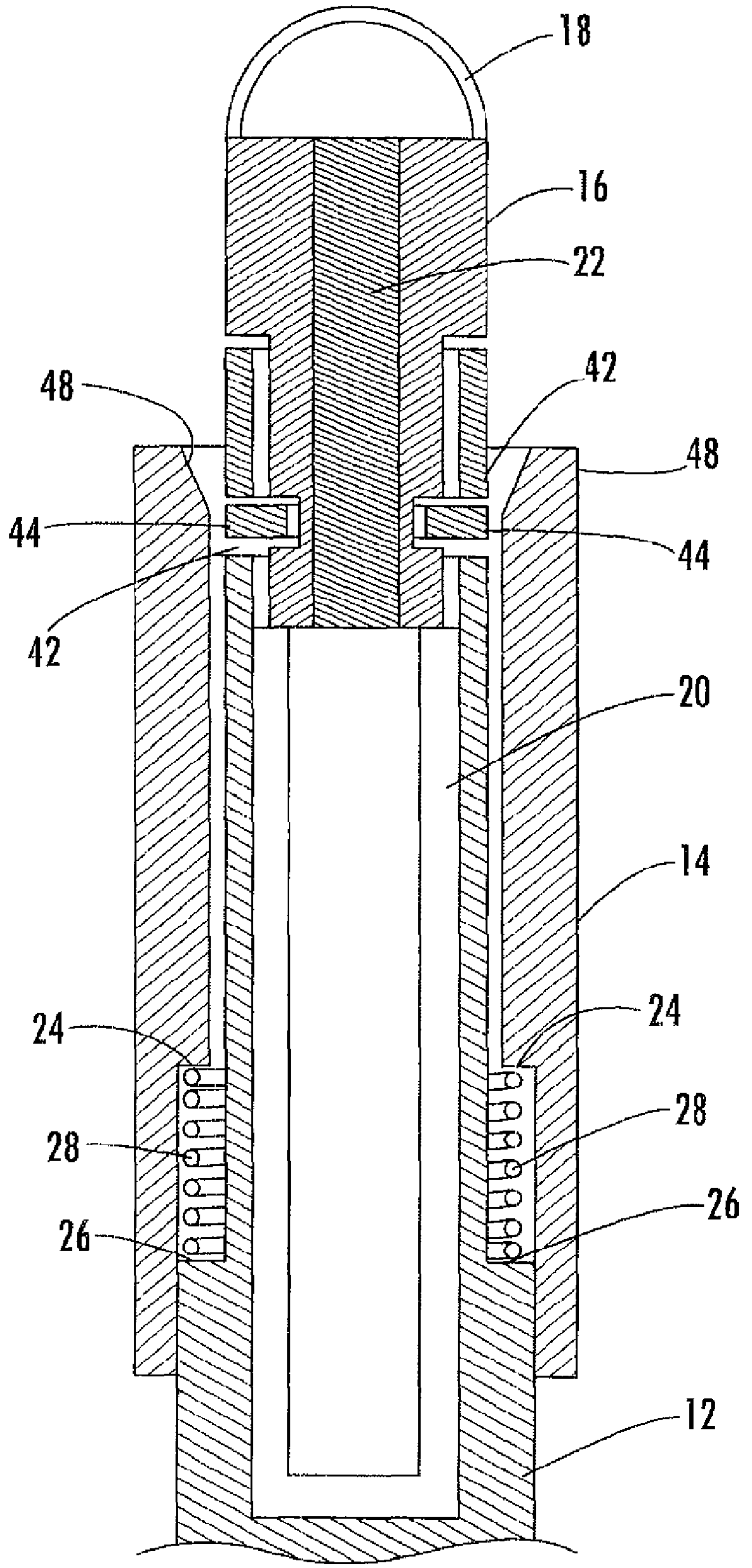
FIG. 3 is a cross sectional view of the shielded radioactive medical container according to a preferred embodiment of the invention.
Figure 4:
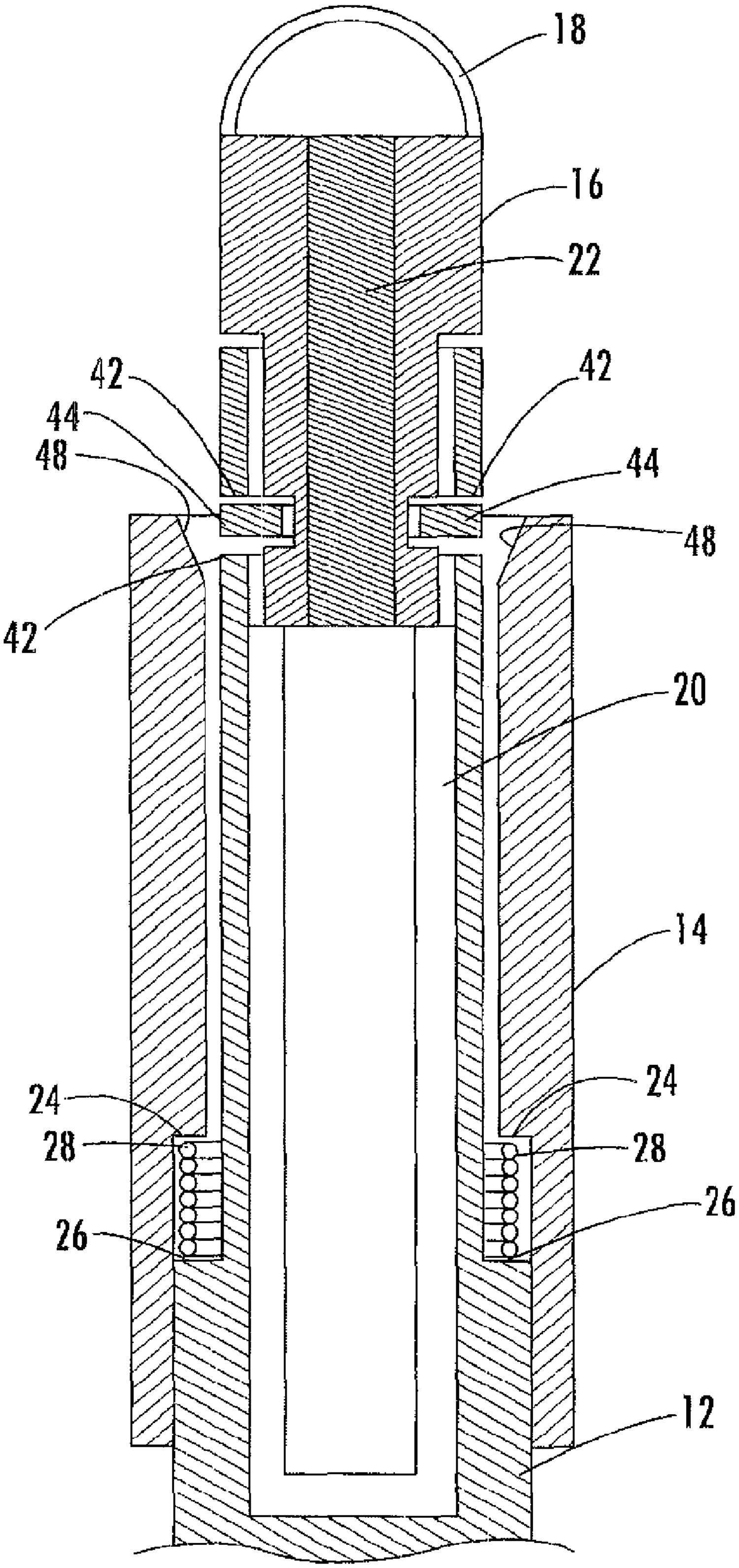
FIG. 4 is another cross sectional view of the shielded radioactive medical container according to a preferred embodiment of the invention.

Collar 14 is located on the exterior of the housing 10. Referring now to FIGS. 3 and 4, the exterior of the housing 12 has a shoulder 26 located proximate the open end. A spring 28 rests on the housing shoulder 26. The collar spring 28 biases the collar 14 towards the open end of the housing 12 by placing a biasing force on a shoulder 24 located on the interior of the collar 14.

The collar 14 operates a quick release mechanism which is preferably a pin and receiver mechanism 40. A plurality of bores 42 are located on the housing 12 proximate the open end of the housing 12. A pin mechanism 44 is located within each the plurality of bores 42. The plurality of pins 44 are formed to fit within a receiver on the quick release cap 16. In a preferred embodiment, the receiver is a groove 46 located on the proximate end 36 of the quick release cap 16. In alternate embodiments the receiver may be bores located in the cap 16 or other devices configured to receive pins.

Pin springs located within the pins 44 bias the plurality of pins 44 away from the groove 46. However, as shown in FIG. 3, when the collar 14 is in the up position, as normally biased by the collar spring 28, the inclined engagement surfaces 48 on the collar 14 engage the plurality of pins 44 and press them into the groove 46 on the quick release cap 16. Thereby, the pin and receiver mechanism 40 secures the quick release cap 16 onto the housing 12 and allows the container 10 to be transported with minimal radiation emitted from the container 10.

When medical personnel desire to remove a radioactive object from the container 10, the process can be done quickly using the quick release mechanism of the present invention. A user pushes the collar 14 into a down position, as shown in FIG. 4. When the collar 14 is in the down position, the pins 44 are biased away from the groove 46 on the quick release cap 16 by the pin springs. The quick release cap 16 may then be quickly and easily removed from the housing 12.

Figure 18:
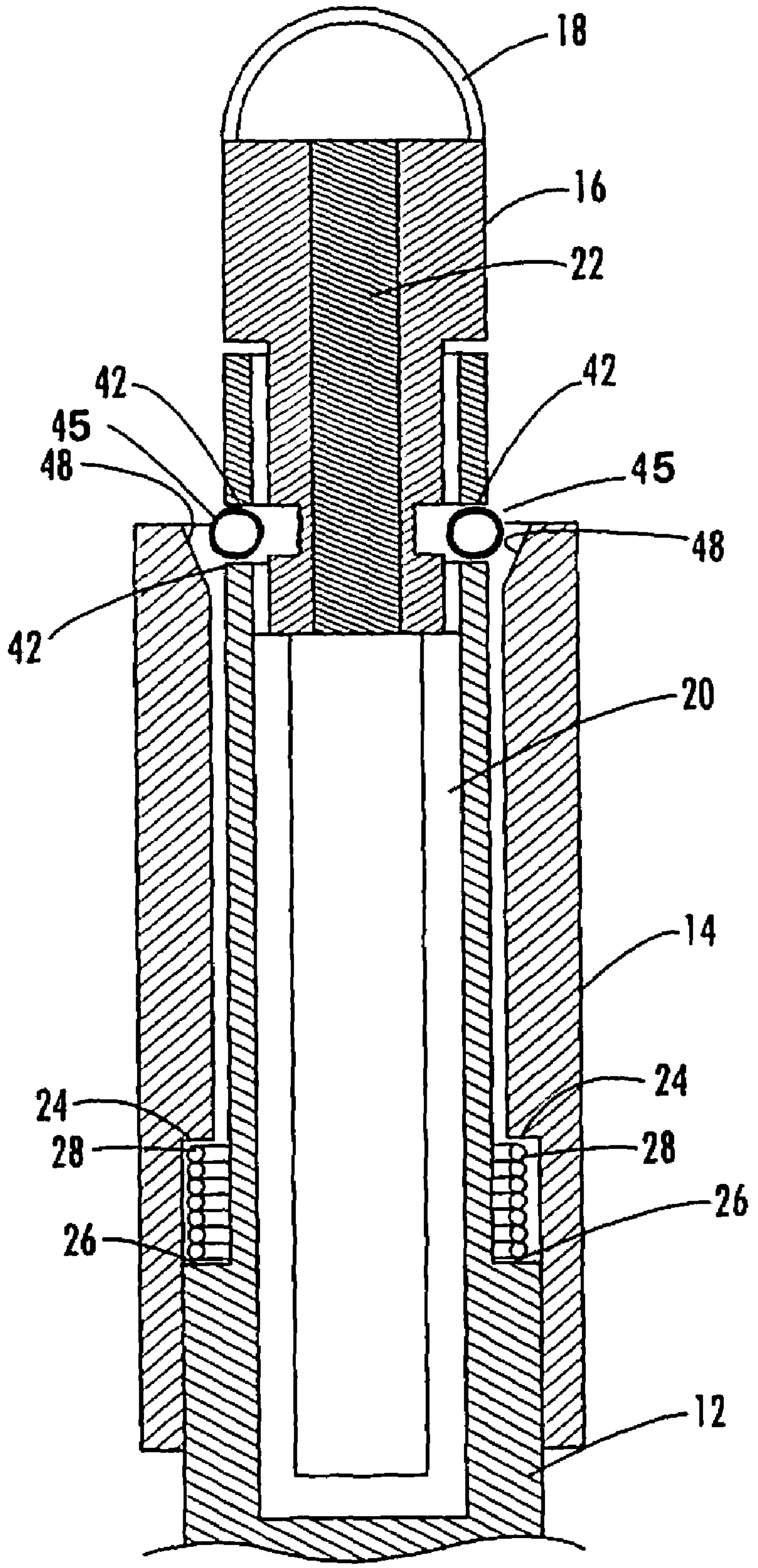
FIG. 18 is a somewhat schematic cross sectional view of the shielded radioactive medical container according to a preferred embodiment of the invention.
Figure 19:
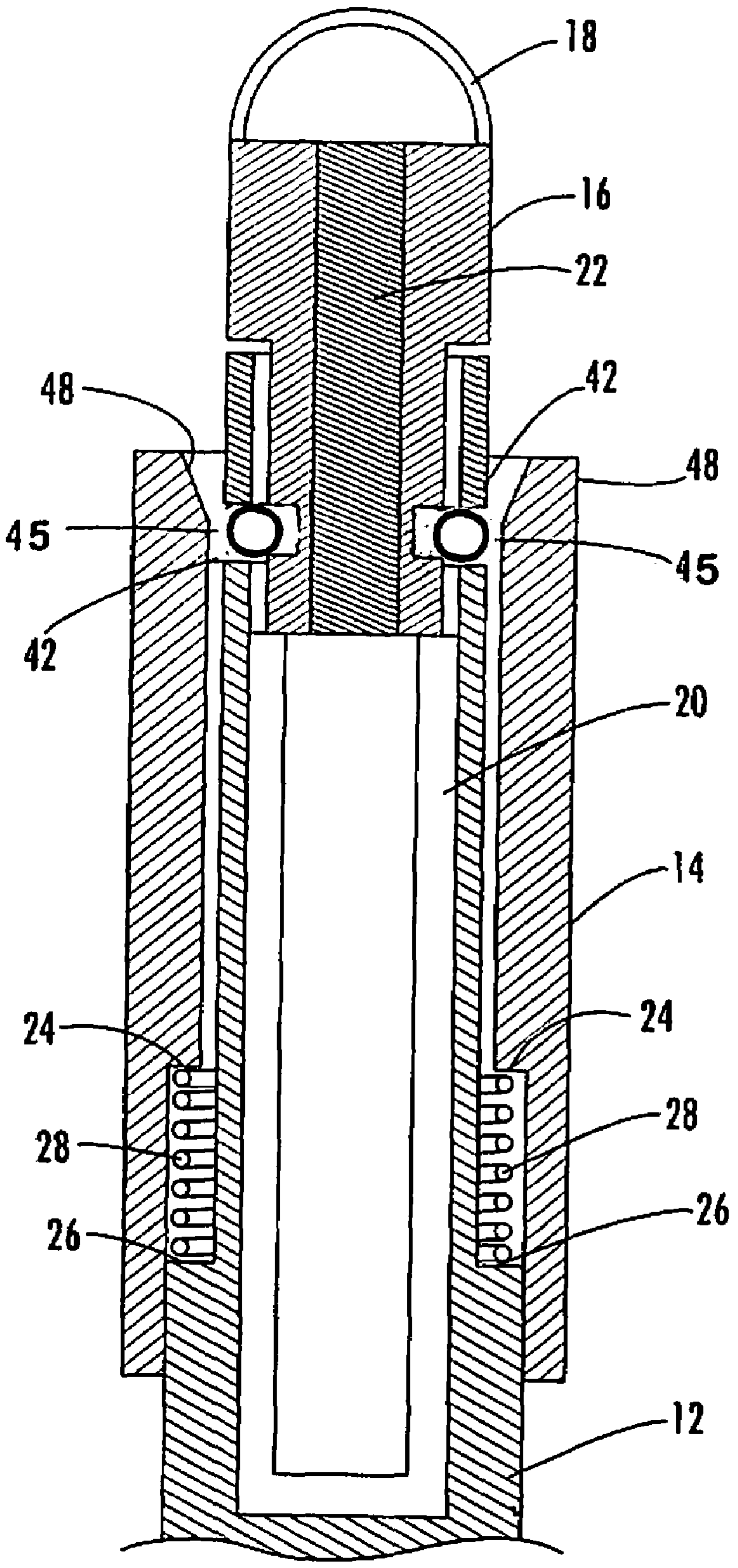
FIG. 19 is another somewhat schematic cross sectional view of the shielded radioactive medical container according to a preferred embodiment of the invention.
Figure 20:
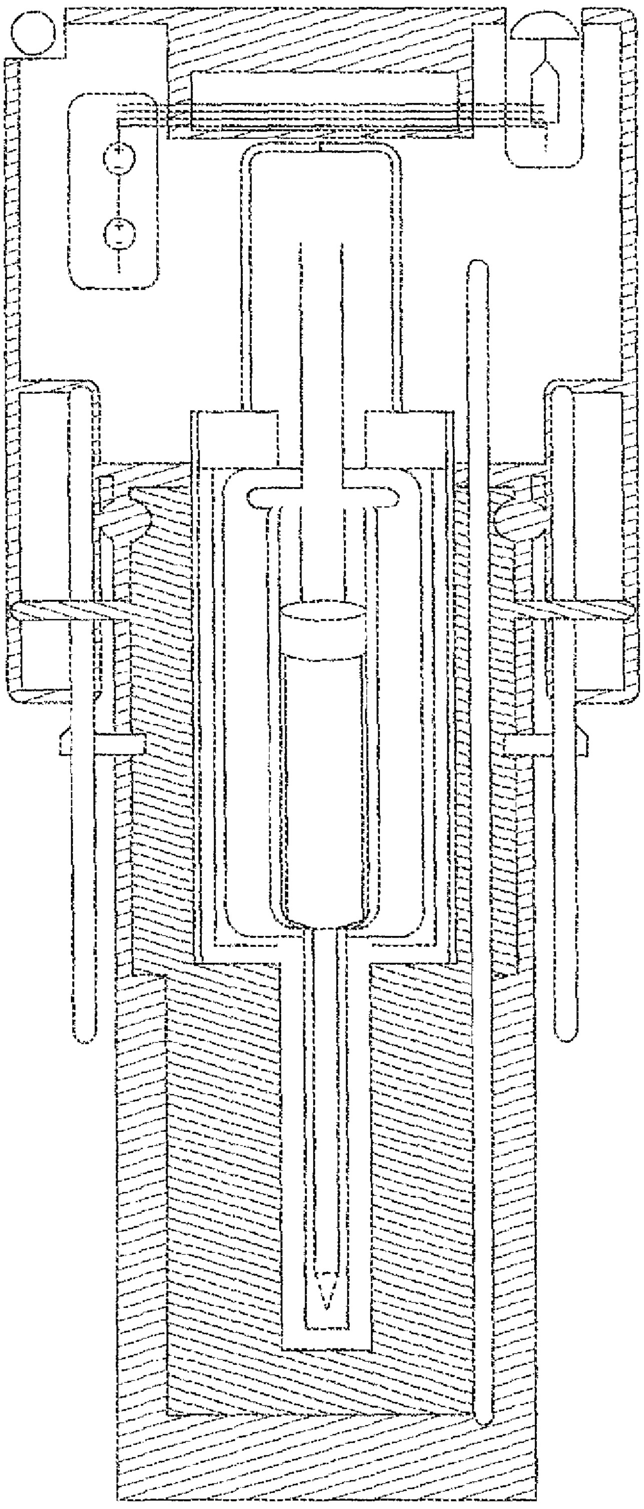
FIG. 20 is a somewhat diagrammatic cross sectional view of a safety data shield, a syringe shield, a syringe, a removable shield cap, and an electronic display device mounted in the cap.

Alternatively, the quick release mechanism may consist of balls 45 movably located in the plurality of bores 42. When the collar 14 is in the up position as shown in FIG. 19, the inclined engagement surfaces force the balls 45 into the groove 46 on the quick release cap 16, holding the cap in place. When the collar 14 is in the down position as shown in FIG. 18, the movable balls 45 are no longer forced into the groove 46 and the quick release cap 16 may be removed.

Figure 7B:
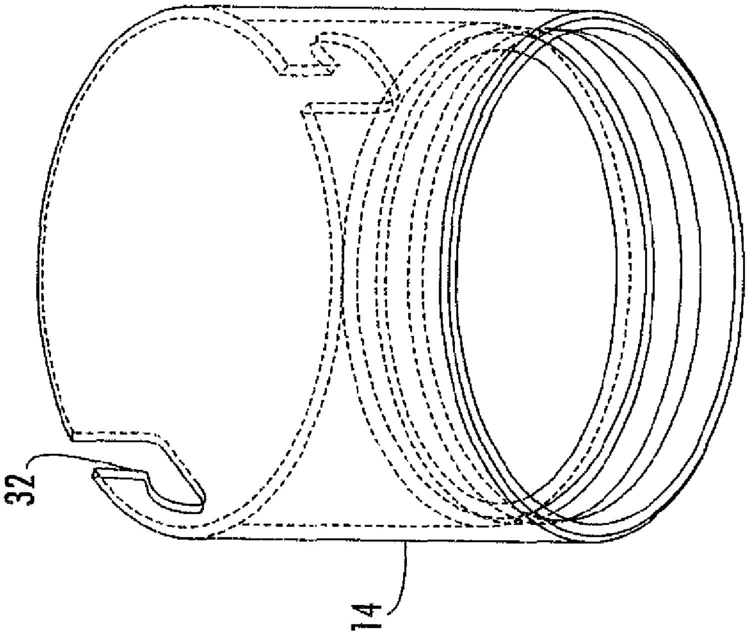
FIGS. 7*a-b* are views of the collar of the shielded radioactive medical container according to a preferred embodiment of the invention.
Figure 7A:
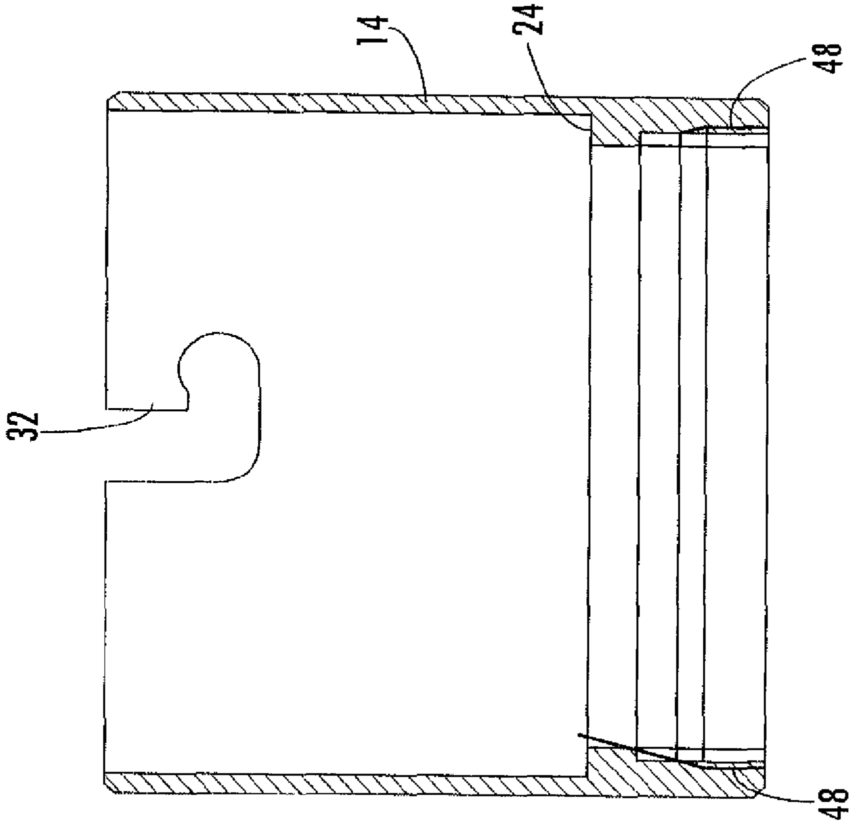

Referring to FIGS. 7A and 7B, a right angled slot 32 is located on the collar 14 which is configured to mate with a protrusion 30 on the housing 12. When a user places the collar 14 in the down position, they may slide the right angled slot 32 onto the protrusion 30 and twist the collar 14, thereby securing the collar 14 in the down position. This allows the user to more quickly and dexterously perform tasks by removing the need for using one hand to keep the collar 14 in the down position. Further, the quick release cap 16 may be quickly replaced back onto the housing 12 when the collar 14 is secured in the down position.

In a preferred embodiment, the handle 18, is a bail handle located on the distal end 38 of the quick release cap 16 and is pivotable on the end of the quick release cap 16. In other words, the handle 18 may be pivoted to a position perpendicular to the distal end 38 of the quick release cap 16, so that the container 10 may be easily carried by medical personnel and the quick release cap 16 may be easily removed. The handle 18 may be pivoted to a position parallel to the distal end 38 of the quick release cap 16, so that the container 10 may be more easily stored. In one embodiment of the invention, the handle 18 may lay in a recess in the distal end 38 of the quick release cap 16.

Figure 8B:
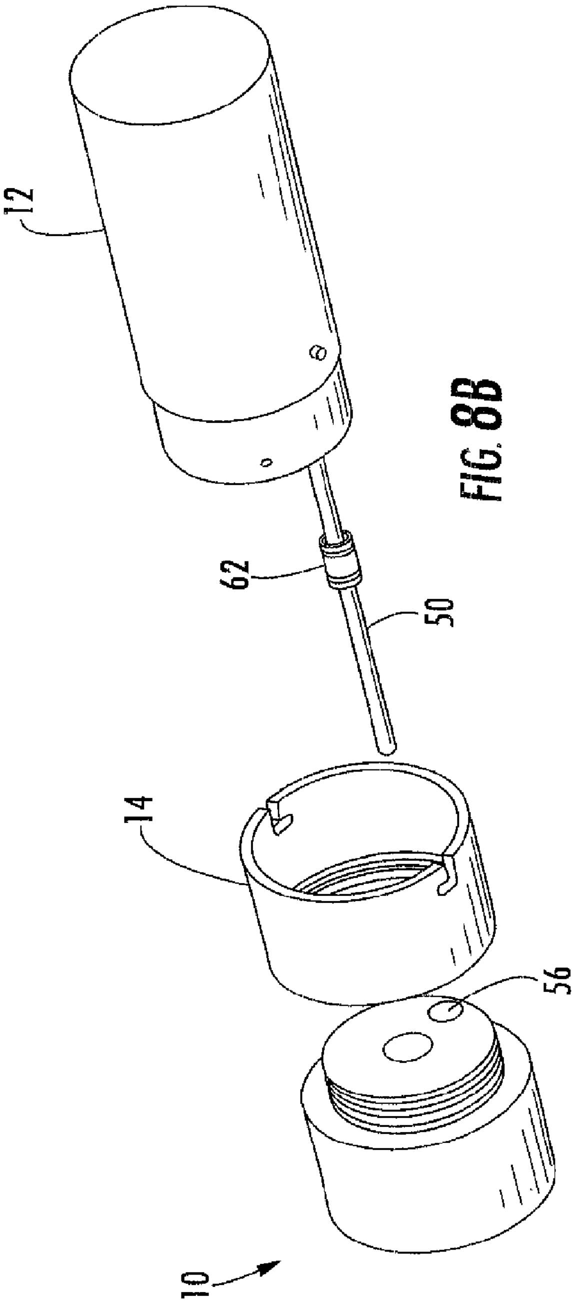
FIG. 8*b* is an exploded view of the shielded radioactive medical container according to an alternate embodiment of the invention.
Figure 8A:
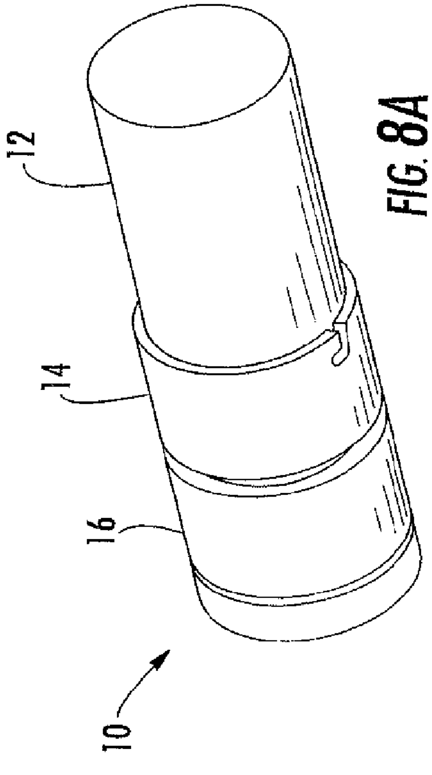
FIG. 8*a* is a view of the shielded radioactive medical container according to an alternate embodiment of the invention.
Figure 9B:
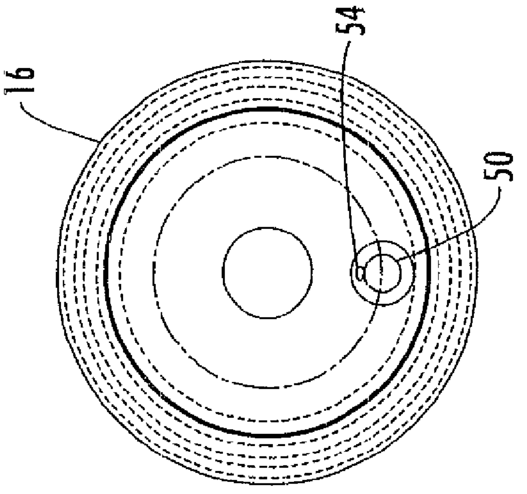
FIGS. 9*a-b* are views of the quick release cap of the shielded radioactive medical container according to an alternate embodiment of the invention.
Figure 9A:
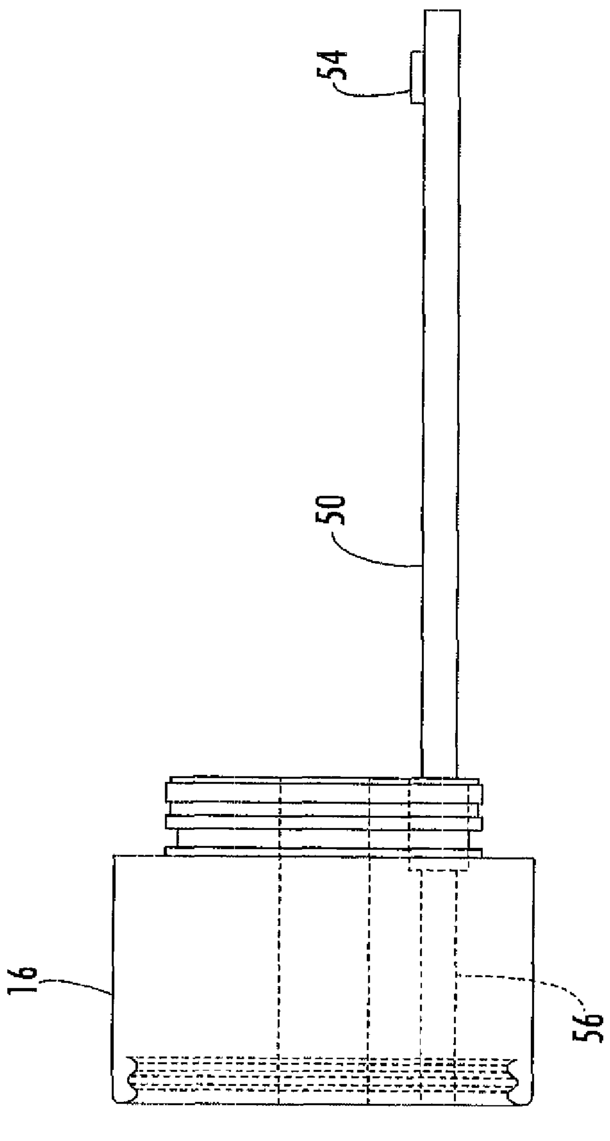

An alternate embodiment of the invention, as shown in FIGS. 8*a* and 8*b*, utilizes a keyed rail 50 located in a slotted cavity 52 to assist in properly removing the quick release cap 16 from the housing, without contacting, and possibly damaging a radioactive object within the container 10. As shown in FIGS. 9*a-b*, a keyed rail 50 is located and securely attached in a rail cavity 56 in the quick release cap 16. The keyed rail 50 extends outwardly from the proximate end of the cap 16 and includes a key 54 proximate the end of the rail opposite the cap 16.

Figure 10C:
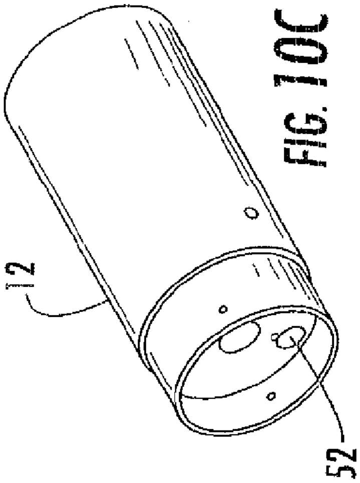
FIGS. 10*a-c* are views of the housing of the shielded radioactive medical container according to an alternate embodiment of the invention.
Figure 10B:
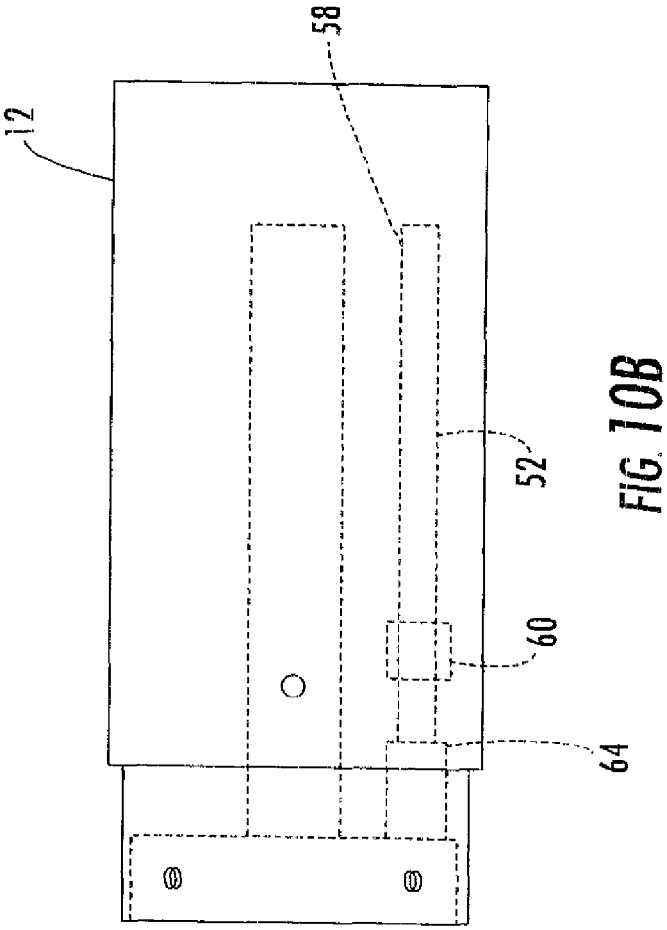
Figure 10A:
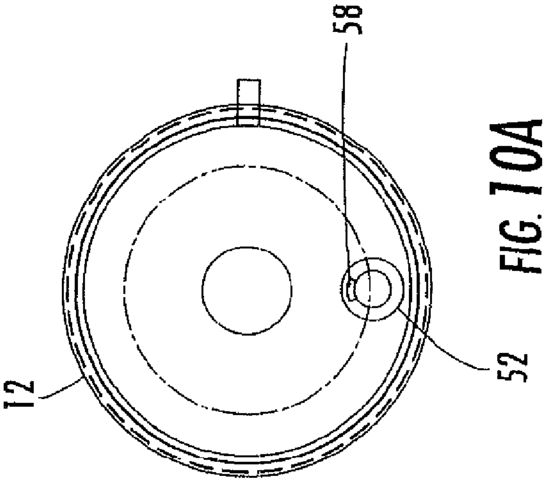

As shown in FIGS. 10*a-c*, the housing includes a slotted cavity 52 having a slot 58 extending along its length. The cavity 52 has an opening 64 in the open end of the housing 12. Guide bearing 62 is located in the opening 64. The slotted cavity includes a cutout 60 proximate the open end of the housing. The keyed rail 50 on the quick release cap 16 is slidably located on the guide bearing 62 in the slotted cavity 52. The key 54 mates with the slot 58 in the cavity 52, which allows the cap 16 to be moved away from the housing 12, while not allowing the cap 16 to rotate about the rail 50. This prevents the cap from contacting the radioactive object located in the interior. When the cap has move outwardly a sufficient distance from the cap and radioactive object, the key 54 is located in the cutout 60, allowing the cap 16 to be rotated, so that the radioactive object may be removed.

Multiple slots may be located in the cavity, allowing the cap 16 to be lowered onto the housing in a position where the cap will not contact the radioactive object. In other embodiments, the rail 50 may be slotted, with a key located in the cavity 52 or the shielded container may utilize other slot/key mechanisms. Further, the rail and cavity may be external to the housing 12, contained within a separate independent housing attached to the shielded container.

Figure 11B:
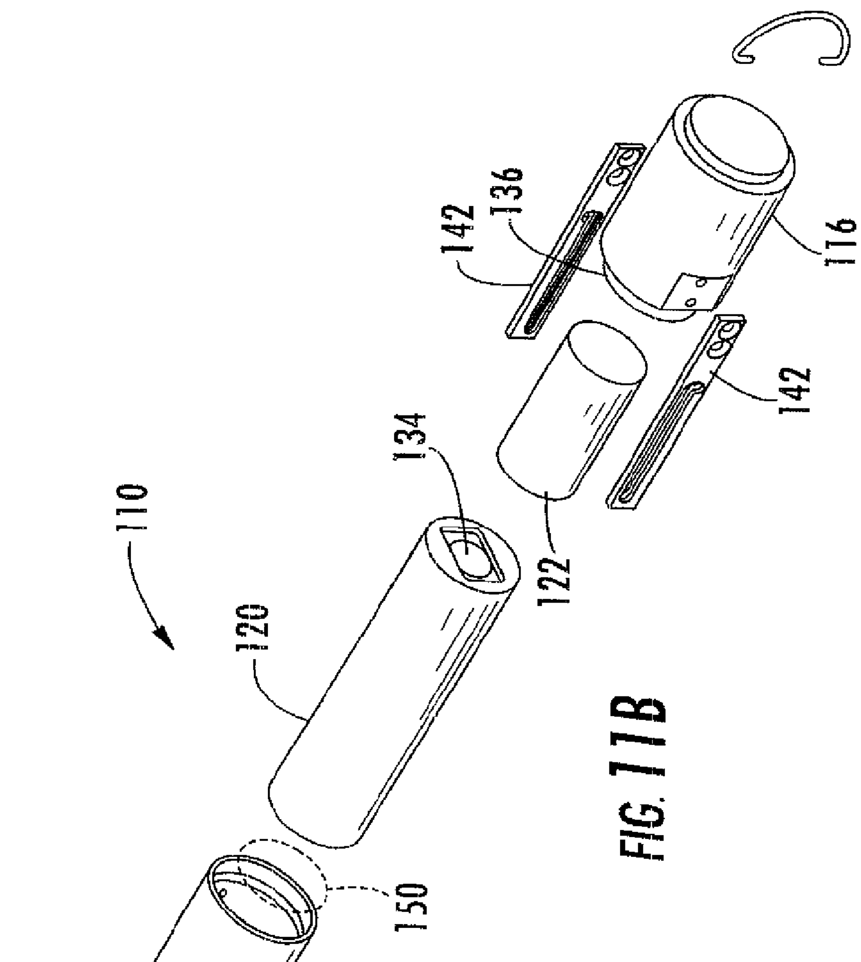
FIG. 11*b* is an exploded view of the shielded radioactive medical container according to a second alternate embodiment of the invention.
Figure 11A:
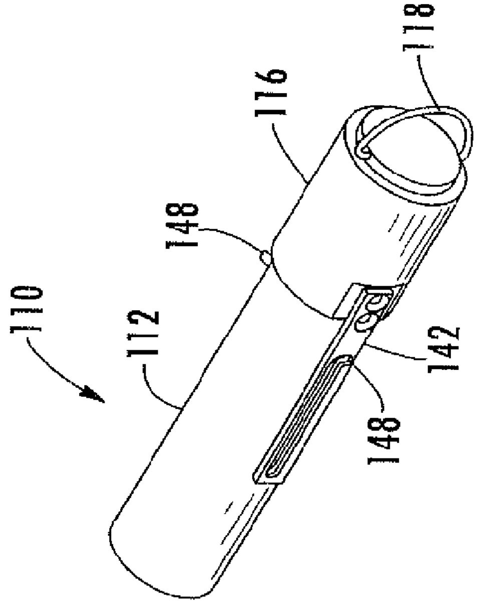
FIG. 11*a* is a view of the shielded radioactive medical container according to a second alternate embodiment of the invention.
Figure 12A:
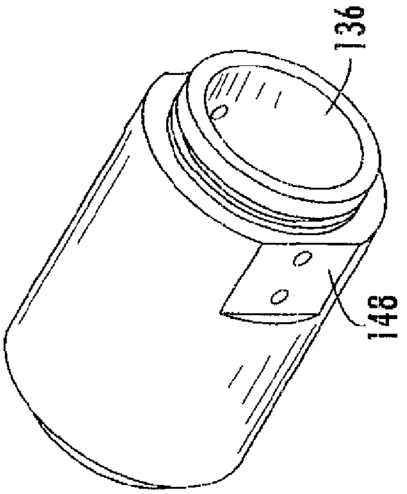
FIGS. 12*a-d* are views of the quick release cap of the shielded radioactive medical container according to a second alternate embodiment of the invention.
Figure 12B:
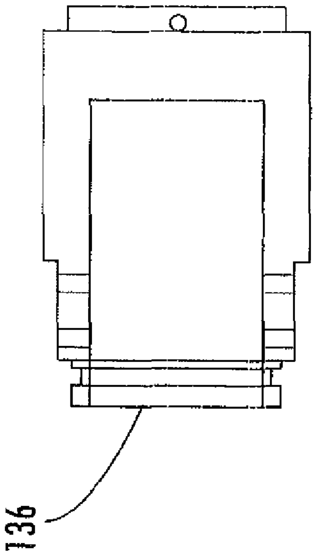
Figure 12C:
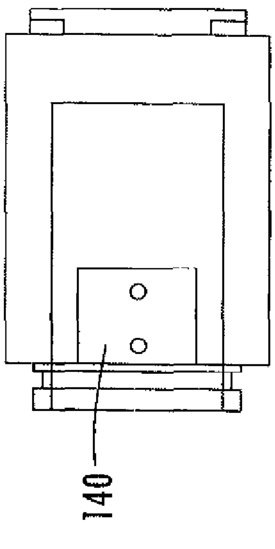
Figure 12D:
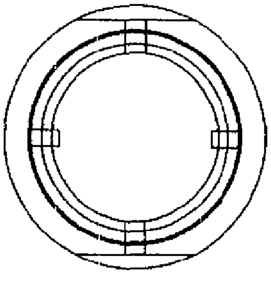

Another alternate embodiment of the present invention is shown in FIGS. 11*a* and 11*b* and utilizes a flip top mechanism as the quick release mechanism. The shielded container 110 of this embodiment includes a housing 112, a quick release cap 116, and a handle 118.

Referring now to FIG. 11*b*, there is shown an exploded view of this alternate of the shielded radioactive medical container 110. The housing is preferably tubular, with a closed end and an open end. The tubular housing 112 is preferably cylindrical, but in alternate embodiments may be a square tube, rectangular tube or any other shaped tube.

Lower shield 120 is located in the interior of the housing 112 and preferably has a tubular configuration to fit snugly within the housing 12. The lower shield 120 has a cavity 134 with an opening which allows a radioactive object to be placed within the cavity 134 from the open end of the housing 112. The cavity 134 is preferably sized to allow a syringe to fit therein. The lower shield 120 may be made of any material which is suitable for shielding radiation, and is preferably lead or tungsten.

The open end of the housing 112 is configured so that the proximate end 136 of the quick release cap 116 fits inside of the housing 112. When the quick release cap 116 is secured onto the housing 112, the proximate end 136 of the cap 116 is located within the open end of the housing 112. An upper shield 122 is located within the interior of the quick release cap 116 and acts as a radioactive shield which closes off the cavity 134 in the lower shield 120 when the cap 116 is secured on the housing 112. The upper shield 122 is preferably cylindrical in shape and made of the same material as the lower shield 120.

Figure 13A:
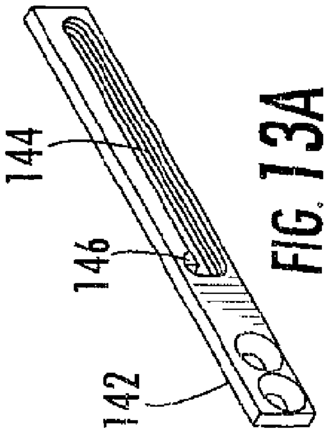
FIGS. 13*a-c* are views of the slotted flip top arm of the shielded radioactive medical container according to a second alternate embodiment of the invention.
Figure 13C:
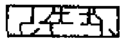
Figure 13B:
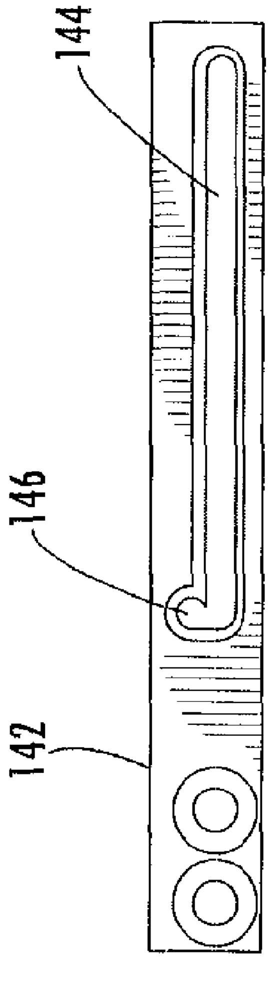
Figure 14B:
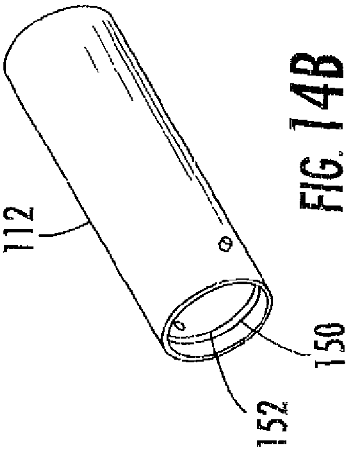
FIGS. 14*a-c* are views of the housing of the shielded radioactive medical container according to a second alternate embodiment of the invention.
Figure 14A:
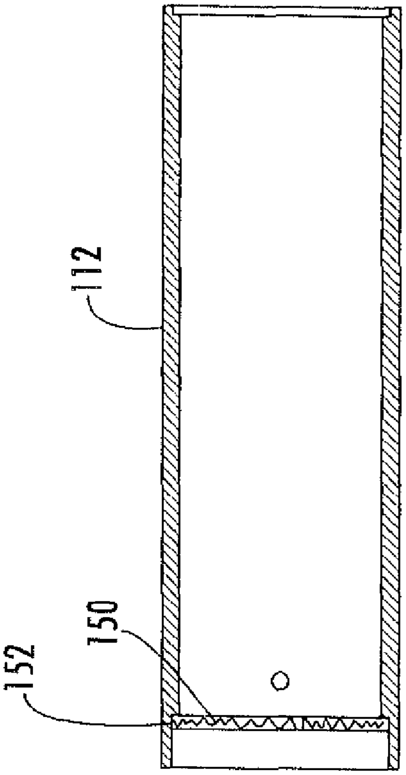
Figure 14C:
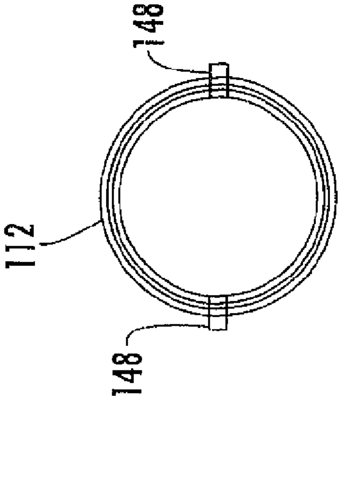

As shown in FIGS. 12*a-d*, the quick release cap 116 has a plurality of level surfaces 140, where a flip top arm 142 (shown in FIGS. 13*a-c*) is attached. The flip top arm 142 has a slot 144 having a right angled portion 146 on the end of the slot 144 closest to the quick release cap 116. Dowels 148 located in bores located proximate the open end of the tubular housing 112 are slidably located in the slots 144 in the flip top arms 142. As shown in FIGS. 14*a-c*, a disc spring 150 is located in the interior groove 152 in the open end of the tubular housing 112 to provide a biasing force against the quick release cap 116 when the cap is secured on the housing.

The flip top arms 142, dowels 148, and disc wave spring 150 act as a quick release mechanism for this alternate embodiment of the invention. When a user desires to close and secure the container 110, the quick release cap is slid into position onto the open end of the tubular housing 112. The quick release cap 116 is then twisted, so that the dowels 148 slide into the right angled portion 146 of the arm's slots 144.

The biasing force created by the disc wave spring 150 holds the dowels 148 in position in the right angled portion 146.

To remove a radioactive object from the container 110, the quick release cap 116 is twisted so that the dowels 148 are no longer in the right angled portion 146 of the slots 144. The quick release cap 116 is then slid up and off of the tubular housing. The quick release cap 116 may then be pivoted to a position allowing the radioactive object to be removed. The quick release cap 116 is thereby easily and quickly removed from the tubular container, allowing improved access to the radioactive object.

Figures 15A, 15B:
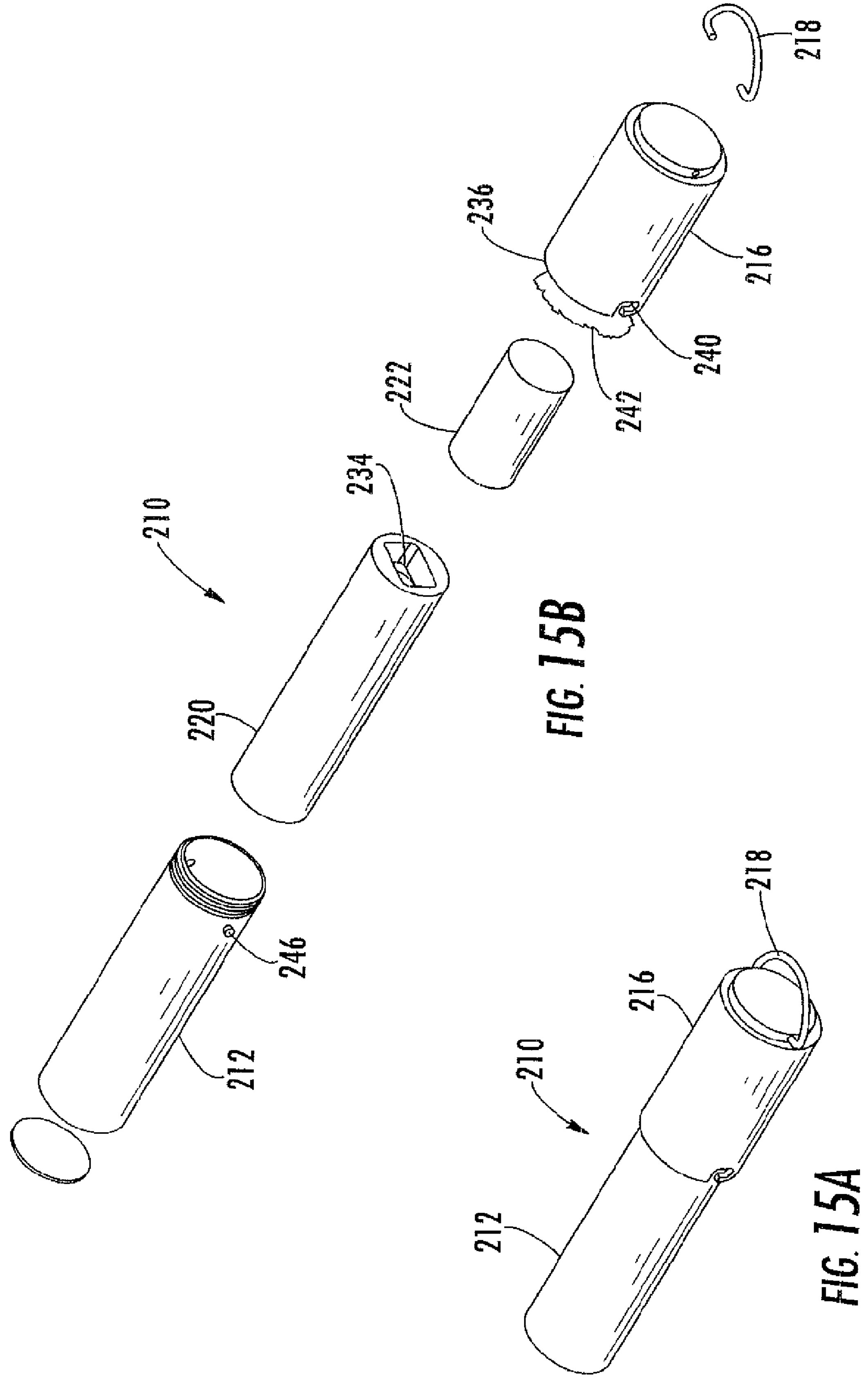
FIG. 15*a* is a view of the shielded radioactive medical container according to a third alternate embodiment of the invention.
FIG. 15*b* is an exploded view of the shielded radioactive medical container according to a third alternate embodiment of the invention.
Figure 16A:
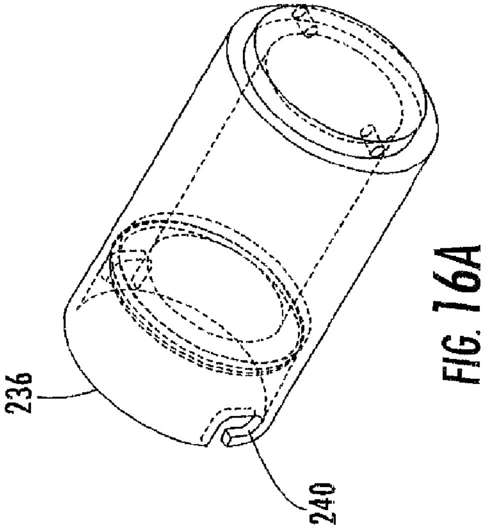
FIGS. 16*a-d* are views of the quick release cap of the shielded radioactive medical container according to a third alternate embodiment of the invention.
Figure 16B:
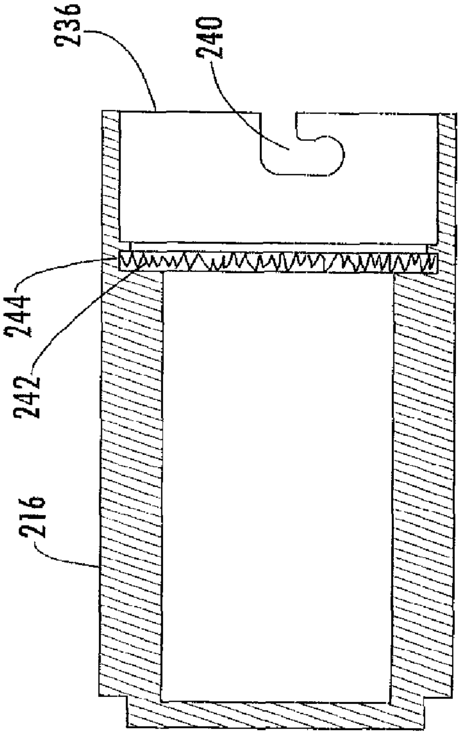
Figure 16D:
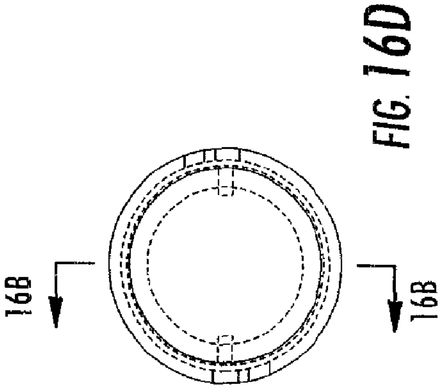
Figure 16C:
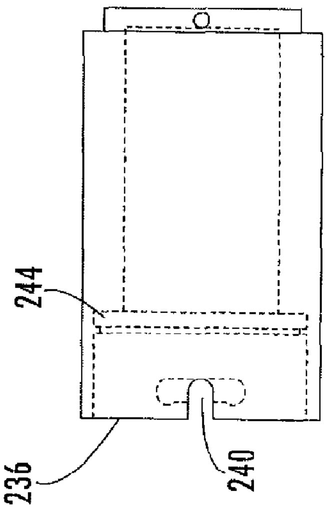

Another alternate embodiment of the present invention is shown in FIGS. 15*a* and 15*b* and utilizes a twist top mechanism as the quick release mechanism. The shielded container 210 of this embodiment includes a housing 212, a quick release cap 216, and a handle 218.

Referring now to FIG. 15*b*, there is shown an exploded view of this alternate of the shielded radioactive medical container 210. The housing is preferably tubular, with a closed end and an open end. The tubular housing 212 is preferably cylindrical, but in alternate embodiments may be a square tube, rectangular tube or any other shaped tube.

Lower shield 220 is located in the interior of the housing 212 and preferably has a tubular configuration to fit snugly within the housing 212. The lower shield 220 has a cavity 234 with an opening which allows a radioactive object to be placed within the cavity 234 from the open end of the housing 212. The cavity 234 is preferably sized to allow a syringe to fit therein. The lower shield 220 may be made of any material which is suitable for shielding radiation, and is preferably lead or tungsten.

The open end of the housing 212 is configured so that the proximate end 236 of the quick release cap 216 fits over the exterior of the housing 212. When the quick release cap 216 is secured onto the housing 212, the proximate end 236 of the cap 216 is located over the open end of the housing 212. An upper shield 222 is located within the interior of the quick release cap 216 and acts as a radioactive shield which closes off the cavity 234 in the lower shield 220 when the cap 216 is secured on the housing 212. The upper shield 222 is preferably cylindrical in shape and made of the same material as the lower shield 220.

Figure 17B:
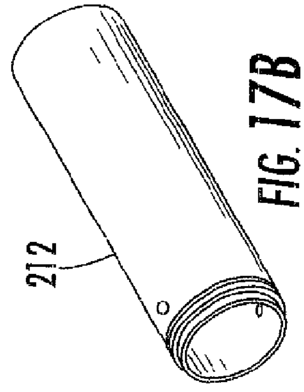
FIGS. 17*a-c* are views of housing of the shielded radioactive medical container according to a third alternate embodiment of the invention
Figure 17A:
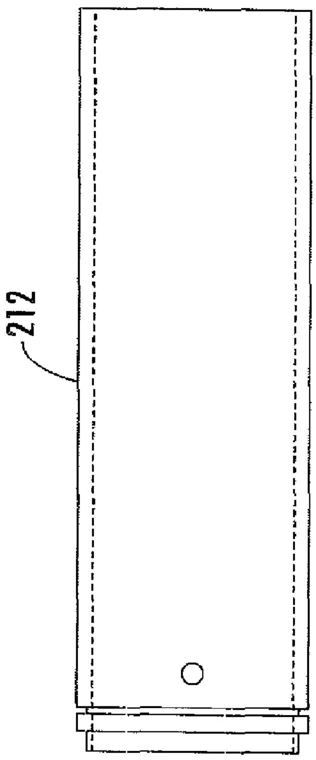
Figure 17C:
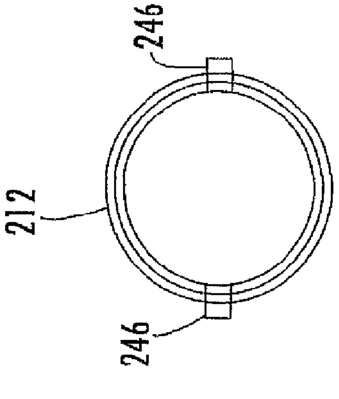

As shown in FIGS. 16*a-d*, a plurality of right-angled slots 240 are located in the proximate end 236 of the quick release cap 216. A disc wave spring 242 is located in the interior groove 244 in the quick release cap and provides a biasing force against the tubular housing 212 when the quick release cap is secured on the housing. As shown in FIGS. 17*a-c*, dowels 246 are located in bores proximate the open end in the tubular body. These dowels 246 are configured to fit within the right angle slots 240 on the quick release cap. The dowels, slots, and spring form the quick release mechanism of this alternate embodiment of the invention.

When a user desires to close and secure the container 210, the quick release cap is placed into position on the open end of the tubular housing 212. The quick release cap 216 is lowered and then twisted, so that the dowels 246 on the tubular housing 212 slide into the right angled slots 240. The biasing force created by the disc wave spring 242 holds the dowels 246 in position in the right angled slots 240.

To remove a radioactive object from the container 210, the quick release cap 216 is twisted and lifted so that the dowels 246 are no longer positioned in the right angled slots 240 on the quick release cap 216. The quick release cap 216 is thereby easily and quickly removed from the tubular container, allowing improved access to the radioactive object.

FIGS. 20-28 illustrated an automated version of the safety shields (medical containers) described above. The automated safety shields are incorporated into a computer system that is integrated into other computer systems, such as computer systems found in pharmacies, hospitals, clinics and doctor's offices. Thus, the automated safety shields enable efficient handling of both the radioactive pharmaceutical and the related information necessary to use the pharmaceutical.

Automated Safety Data Shields

Over 13,000,000 unit doses of radioactive pharmaceuticals are administered in the US each year for the management of a variety of diseases that employ nuclear medicine techniques in their diagnosis, staging, and/or treatment. The inherent nuclear properties of these materials result in their on-going loss due to radioactive decay processes that by their very nature provide the necessary radiations that enable their diagnostic and/or therapeutic applications in nuclear medicine. These same nuclear properties, however, require that certain precautions be strictly followed in the handling and use of these unique pharmaceuticals in order to protect personnel and staff from excessive exposures to radiation.

The current shielding and packaging systems and products used to transport and handle radioactive pharmaceuticals are flawed in two primary respects: a) shielding components are not integrated, thus requiring personnel to unshield radioactive sources and place it into individual and different devices for the dispensing and packaging, transportation, patient delivery, and administration of the desired radiopharmaceutical, and b) though considerable information regarding the radiopharmaceutical are processed and recorded using relatively sophisticated data management programs, much of critical data associated with the radiopharmaceutical identity and its disposition are still tracked manually and in hard-copy form, with key information entered at some point following the administration of the drug. In this manner, timely information relating to the amount of radioactivity contained in a unit dose at any given moment must be manually calculated relative to the half-life of the radioactive material, and the time of actual administration (and quantity administered) are necessarily recorded first by hand, and then later entered into the patient's data file. Both these actions are subject to human errors, and inaccuracies associated with manual processing of data and its notation.

The Current Situation—Patient and Radiopharmaceutical Information and Channels/Points Process at Hospital—Initiation of Patient Dose Data The hospital nuclear medicine department typically initiates the process leading to the dispensing of a unit-dose, patient-specific radiopharmaceutical from an off-site dispensing radiopharmacy by providing the disposing pharmacist with the following specific information as may be required for the daily requirements of their nuclear medicine patients: a. Patient Identity b. Radiopharmaceutical requirements Name of radiopharmaceutical Amount of radioactivity required Prescribing physician Time of desired administration (i.e., 'calibration' time)

Hospital personnel often verbally transfer information to dispensing radiopharmacy, though greater use of electronic transmission of hospital data to dispensing radiopharmacy is occurring.

Essential equipment used in the process of 'filling' prescriptions for radiopharmaceuticals includes: Radionuclide dose calibrator(s) (for measuring the amount of radiopharmaceuticals), sturdy transport cases with syringe transport shields (shields for 'over-the-road' transportation of syringes from the dispensing pharmacy to the hospital), syringe carrier shields (for handling syringes containing radioactive to patient administration areas), syringe injection shields—used to safely contain syringes during patient administration, a computerized radiopharmacy information system (RxIS) (usually provided by dispensing radiopharmacy to hospitals for the purpose of tracking and processing salient information about the radiopharmaceutical, including its receipt and disposition).

Dispensing Pharmacy—Filling Prescription for Nuclear Medicine Patients

At the dispensing pharmacy, current Rx Information Systems (RxIS) serve as dispensing programs that calculate the up-to-date amounts of the radiopharmaceuticals, manage quantities of radiopharmaceutical in inventory, matches hospitals' patients' requirements with product availability, creates hard copy labels of individual prescriptions and records of aggregate prescription data, prepares shipping manifest with bar coding, and creates billing records for hospital customers. Upon entering hospitals' patients' information and dose needs, the RxIS determines: a. Radiopharmaceutical to be dispensed b. Radiopharmaceutical identity (lot number, compounding data, etc.) c. Amount and volume of desired radiopharmaceutical at intended time of administration Dispensing pharmacist removes (or 'draws') the specified volume of the desired radiopharmaceutical into a unit dose syringe, then—using a radionuclide dose calibrator—he/she assays (i.e., measures) the amount of radioactivity in syringe at that moment, and determines the future value of the dose at the intended time of administration as the amount of radioactivity remaining beyond the appropriate decay interval. This value is obtained either by calculations performed by the dispensing radiopharmacy RxIS program, or by an operator-assisted program on the radionuclide dose calibrator. In all situations, the dose calibrator discriminates only the amount of radionuclide present, a process that is based upon specific nuclear properties of the radionuclide. The dose calibrator does not identify the specific radiochemical form of this radioactive element. In medical practice, it is the complex of the radionuclide in the desired radiochemical form that constitutes the radiopharmaceutical identity that affords the properties of biological distribution.

With the proper amount of desired radiopharmaceutical contained in the unit dose syringe, a hard-copy prescription label is printed that generates a record of: a. Patient Identity b. Hospital Identity c. Radiopharmaceutical Identity Name of Radionuclide Amount contained at intended time of administration Intended time of administration, date Volume contained Prescription number (generated by pharmacy MIS) d. Radiopharmaceutical expiration time The dispensing radiopharmacy places each syringe into a transport shield (usually manufactured of lead or tungsten), and labels the exterior with a hard copy of the prescription data. The syringe transport shield is packaged in a transport container (that holds multiple syringe transport shields) to be delivered to the customer hospital by courier personnel.

Hospital—Receipt of Prescribed Radiopharmaceuticals, Administration, Recordkeeping, Return Presently, at the hospital, personnel check in each patient dose, usually by first swiping the corresponding bar code that reconciles patient dose information into the hospital's RxIS data management system. The transport shield is usually opened at this point, and the syringe is transferred to the syringe carrier shield that is used to safely contain the radioactive syringe to the patient's side. Once at the patient side, the syringe is removed once more and placed into a smaller injection shield that is used to shield the person performing the patient administration. The staff member records the time of patient administration (a critical factor that affects the timing of the patient's scan to be performed later), and—at some later time—manually enters this information into the patient's nuclear medicine database, along with the identity of the person performing the actual administration. The spent syringe is removed from the injection shield, transferred back to the in-house syringe carrier shield. Eventually, the syringe is re-packaged into the original transport shield that is finally returned to the dispensing radiopharmacy. Each syringe transfer containing the radioactive dose from one container to another or from one container to a shield and back again results in additional radiation exposure to hospital staff.

The ORTG Radiopharmaceutical Dose Containment System

The ORTG Dose Containment System is an integrated line of products which encompasses the spectrum of safety shielding and radiopharmaceutical information from the initial dispensing of the product through its transportation from the pharmacy to the user hospital, its disposition, and the subsequent return of the spent syringe to the dispensing nuclear pharmacy. The system products utilize superior component design and fabrication, that couples with new technology to maintain up-to-date information on the radiopharmaceutical dose, all in a convenient package concept that maintains personnel radiation exposures to their lowest achievable levels.

The products include the following:

a. SafetyDATA Shields (SDS) b. Shipping/transport cases for SDS units c. Wireless interface between SDS and Radionuclide Dose Calibrator or MIS SafetyDATA Shields Referring to FIGS. 20-22, the SafetyDATA Shield is a unit dose syringe transport shield that safely contains unit doses of radioactive pharmaceuticals from the point of dispensing entirely to the patient's side and administration.

The SafetyDATA Shield (SDS) is designed with two novel features that favorably address user convenience and lower personnel exposures while allowing users to determine, reconcile, and document certain critical patient-specific data by electronic means in an automated fashion. The SDS's data module—a proprietary microprocessor with an LCD coupled to wireless [in this embodiment, an InfraRed (IR)] communication component—is initially loaded by the dispensing pharmacist with the relevant dose-specific digital information that is subsequently displayed on the SDS's battery-powered LCD screen located on the face of the top of the unit. The dose-specific information uploaded by the pharmacist includes, but is not limited to, the following information about the radiopharmaceutical contained within the SDS: Patient identity, Prescription number, Prescription Name of radionuclide and chemical form, Amount of dispensed radioactivity, and Hospital identity.

Figure 21:
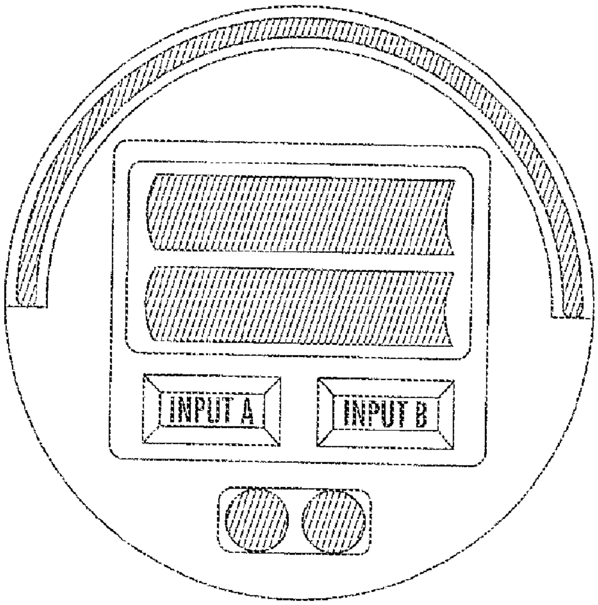
FIG. 21 is a top view of the cap for the safety shield showing the electronic display.
Figure 24:
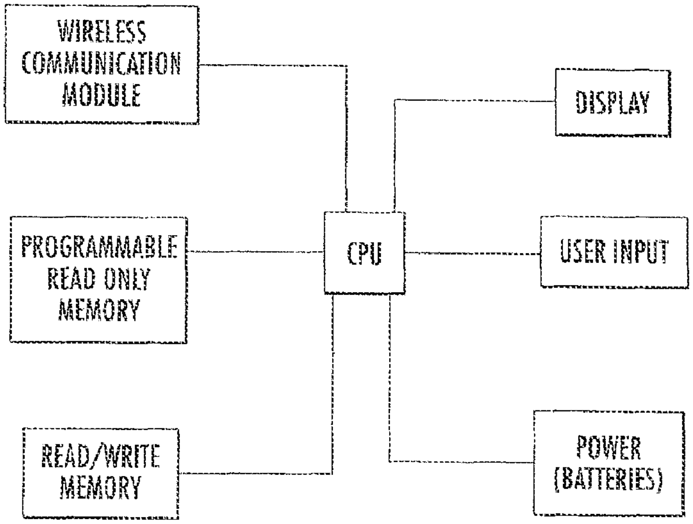
FIG. 24 is a block diagram of the electronics contained within the cap of the shield.

Referring to FIG. 24, a block diagram of the electronic data module is shown. It includes a central processing unit (CPU) that is preferably a microprocessor but could also be a special purpose chip, such as an ASIC. The CPU is connected to a user input which is preferably buttons as shown in FIG. 21. The CPU also controls a display to which it is attached. As the user provides inputs through the user input, the display may change. For example, as the buttons are pushed, the display will rotate through a variety of different types of data that may be of interest to the user.

A power supply is connected to the CPU and it is preferably one or more batteries providing a DC power.

To communicate with other computer systems, such as a hospital computer system or a pharmacy computer system, the CPU is attached to a wireless communication module that is also mounted in the cap of the safety shield along with the CPU. In a preferred embodiment, the wireless module communicates by infrared light, but it could also be a wireless radio communications system, another type of wireless communication, or even a wired communication system.

A programmable read only memory is also provided in the cap of the safety shield connected to the CPU. A semi-permanent program is stored within the programmable read only memory along with other data that is repetitively used by the CPU, including its operating system. If any of this semi-permanent data or other information changes, the programmable read only memory may be reprogrammed to include the new data or the new program. More transient data is stored in a read-write memory that is also connected to the CPU. The read-write memory stores information such as the prescription number, a prescription, patient name, workers in a hospital that might be administering the dose, etc. Preferably, the read-write memory is stable and will not lose its memory in the event of a power failure.

The amount of radioactivity contained in the unit-dose syringe is measured initially by a radionuclide dose calibrator and is loaded via wireless IR into the data module. This information is manipulated by programmed logic in the SDS specific for the individual radionuclide's decay characteristics. In this manner, the amount of radioactivity in the contained radionuclide is continually updated and displayed in real-time on the SDS's LCD. Preferably, the data module stores a decay constant for each radionuclide that may be used. The prescription will include the identity of the radionuclide, and using that information, the data module calculates the current amount of radioactivity based on the initial radioactivity, the decay constant, and the decay equation: a) A=A.sub.0e.sup.—.lamda.t where A.sub.0=initial activity, b) .lamda.=the decay constant c) t=time, and A=the current activity which is displayed.

Upon receipt of the SDS by the hospital, the dose-specific information in the data module is conveyed by wireless IR to the hospital's RXIS or data management program. In this manner, electronic reconciliation of critical dose information with the user's RxIS or data management systems occurs, all without opening the SDS, or removing the radioactive dose from its shield. While dose data is being read into the user's data system, other information regarding the identity of individuals who may potentially administer the radiopharmaceutical is taken from the user's RxIS or data management program and placed into the SDS data module for later recall and logging.

Figure 28:
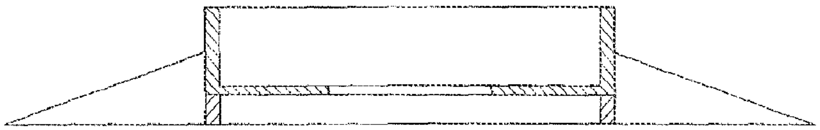
FIG. 28 is a cross sectional view of a base for a canister.

The SafetyDATA Shield—set within a novel slip-fit base (FIG. 28) (which enables stability in the upright position), and a built-in easy-carry bail—contains the patient unit dose all the way from the dispensing pharmacy to the patient's side, without the necessity of opening or further handling of an unshielded dose prior to patient administration. For over-the-road transportation, the SDS is shipped in its matched ORTG transport case, and all ORTG products comply with necessary regulatory guidelines for use and transportation. Referring to FIG. 28, a side cross sectional view of the slip fit base for the canister is shown. In this embodiment, the well of the canister would be circular in a top view and has a diameter of three and one-half inches, which is precisely the diameter of a standard canister. The well lightly grips the bottom of the canister and holds the canister in an upright position. The base is preferably 7½ inches in diameter and also has a circular shape in a top view. The increased diameter of the base as compared to the well creates greater stabilization for holding the canister in an upright position and thereby enables less handling of the canister, which results in less exposure and more convenience. While the preferred dimensions and shapes have been shown, it will be understood that the base diameter, overall height, and well diameter may vary depending upon the application. Also, while a circular base and well is preferred, the base could be other geometric shapes, such as square or polygon shaped cut to sleep. If the canister had a different cross sectional shape, such as a square or polygon cross-section, the well would likewise have a different shape corresponding to the shape of the canister. Therefore, FIG. 28 represents a side cross-section of a base having either a circular or a polygon shape when viewed from the top.

Figure 25:
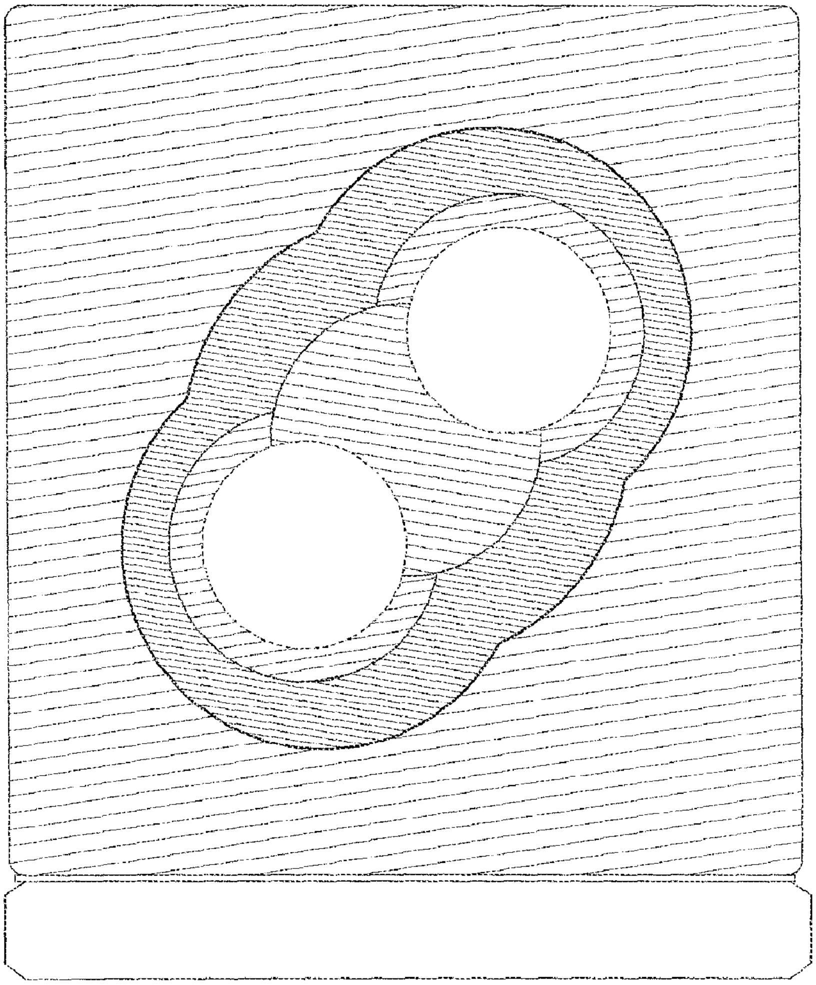
FIG. 25 is a is a top view of a transport case for one, two or three shielding canisters.
Figure 26:
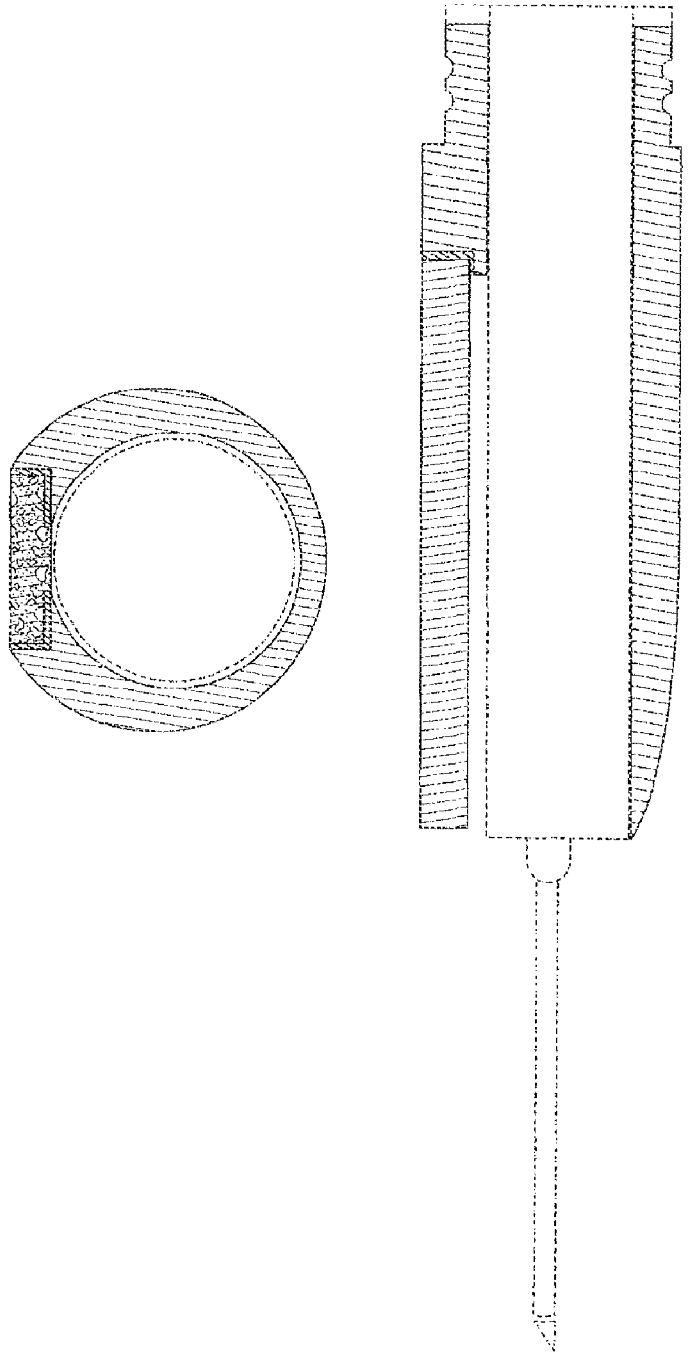
FIG. 26 is a side cross sectional view and a top cross sectional view of a syringe shield.
Figure 27:
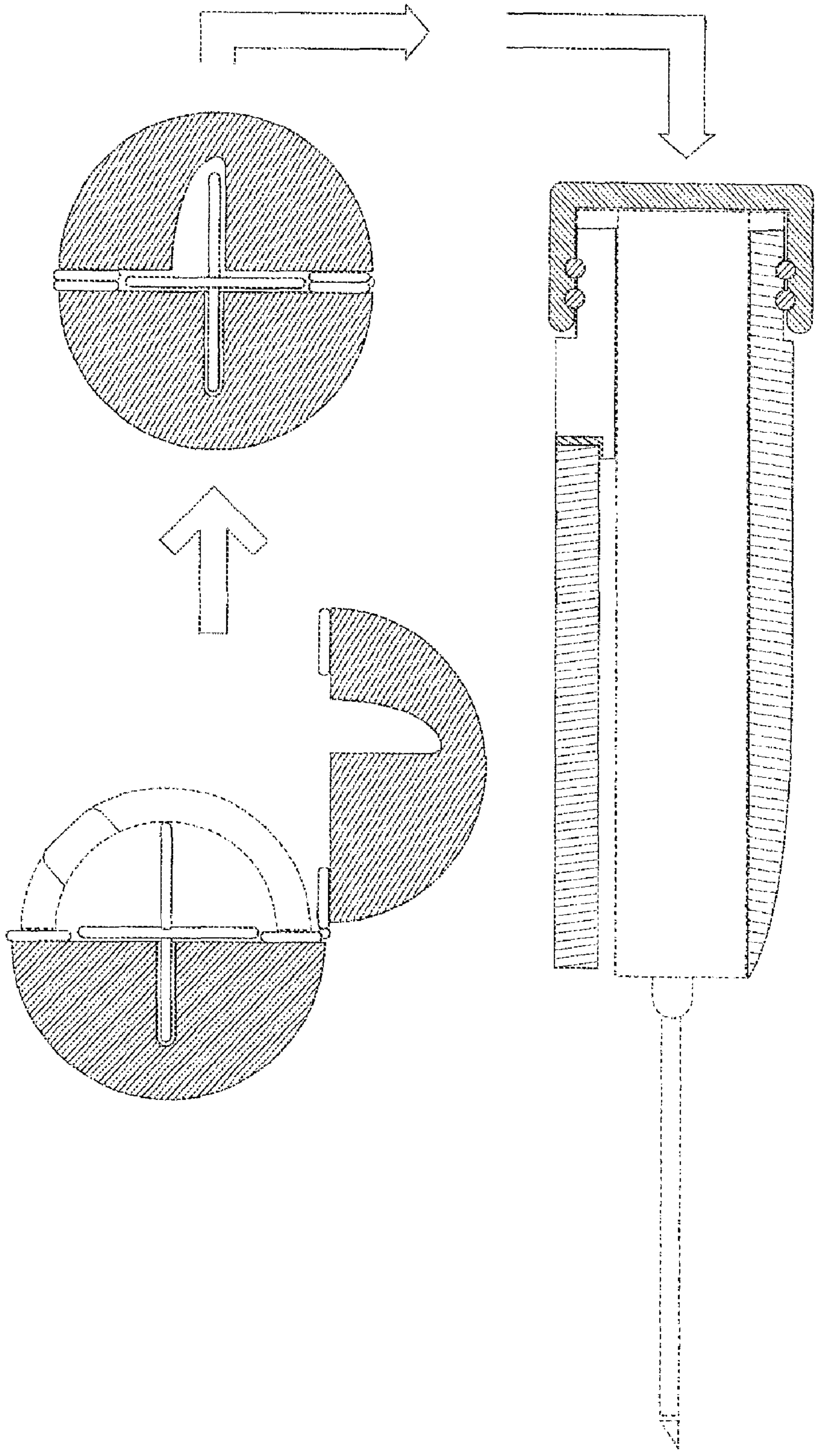
FIG. 27 shows three views of the syringe shield, one showing a longitudinal cross sectional view and two showing end views.

Referring to FIG. 25, a top view of an open transport case is shown. In the this exemplary case, the transport container is square in cross section and includes an outer layer of protective foam, and a radioactive shield is disposed immediately within the outer layer of foam. Within the radioactive shield, a foam socket is provided for carrying one or two canisters (safety shields). When one canister is used, it is placed in the central opening which is configured to hold the canister and prevent it from shifting laterally. If two canisters are being used, they are placed in the openings that are spaced apart on opposite ends of the foam socket. Again, the two outer openings are configured to prevent the canisters from shifting laterally. A lid, which is shown in the open position in FIG. 25, is attached by a hinge to the transport container. Preferably, the lid includes radioactive shielding, such as a lead shield. When the canisters have been inserted into the foam socket, the lid is closed and it is ready for transportation.

Upon opening at the patient's side, a simple turn of the SDS cap (less than ½" rotation) rapidly releases the cap while an internal strut (FIG. 20) ensures that the cap remains attached its matched base such that the unique dose information in the data module and LCD are never separated from the original carrier. The strut prevents contact of the cap with the syringe plunger, thus minimizing spill potential.

A further refinement of the SDS is a specially designed tungsten injection syringe shield (FIGS. 20, 26 and 27) into which the dispensing nuclear pharmacist secures the unit dose syringe before being loaded into the SDS. The tungsten shield, now containing the unit-dose syringe is withdrawn from the SDS only at the desired moment of administration, and acts as a continuously effective personnel shield for the technologist/physician administering the radiopharmceutical. This feature eliminates the need for the technologist/physician to unload a "hot" syringe from a conventional transport/shipping container and insert the syringe into a separate syringe carrier shield at the hospital, or an injection shield at the patient's side. Advantages regarding cumulative personnel exposure are significant.

Upon completing the administration of the radiopharmaceutical, the person performing this task presses in sequence one of the buttons (such as button A in FIG. 21) located on the data module until his/her identity (initials) appears on the LCD, whereupon he/she simultaneously keys both buttons thereby locking in all dose data, including: the time of radiopharmaceutical administration, the precise amount administered, and the identity of the person administrating the drug.

Immediately after injection, the spent syringe, still within the injection shield is returned into the SDS, and the cap is secured onto the base. Before placing the SDS back into the ORTG shield transport container, all electronically 'locked' dosage data is transferred back through the hospital's MIS by wireless IR upload of stored data that links and reconciles the information to its proper location in the user's data RxIS or management program. In this manner, the generation of hand-written, or hard-copy documentation, is no longer required, with all information handled via electronic storage and transfer to similar devices and programs as required to render a final and appropriate record and report.

SDS Models:

The SDS units preferably include four models—A, B, C and D—each designed to appropriately shield radionuclides based upon their critical nuclear properties. Additionally, each model will accommodate either a 3 or 5 cc syringe.

Figure 22:
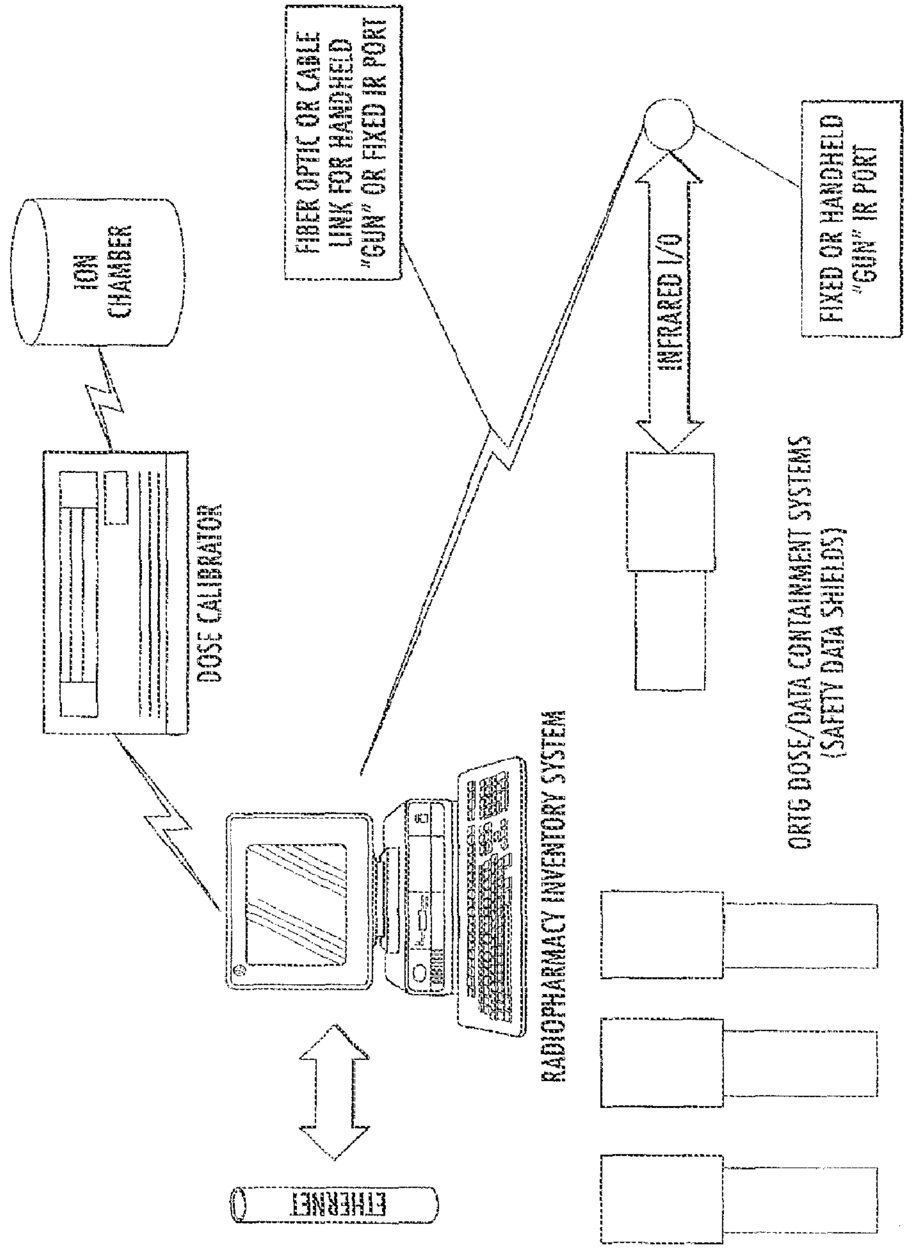
FIG. 22 is a diagram of a system for dispensing and distributing radioactive medicine.
Figure 23:
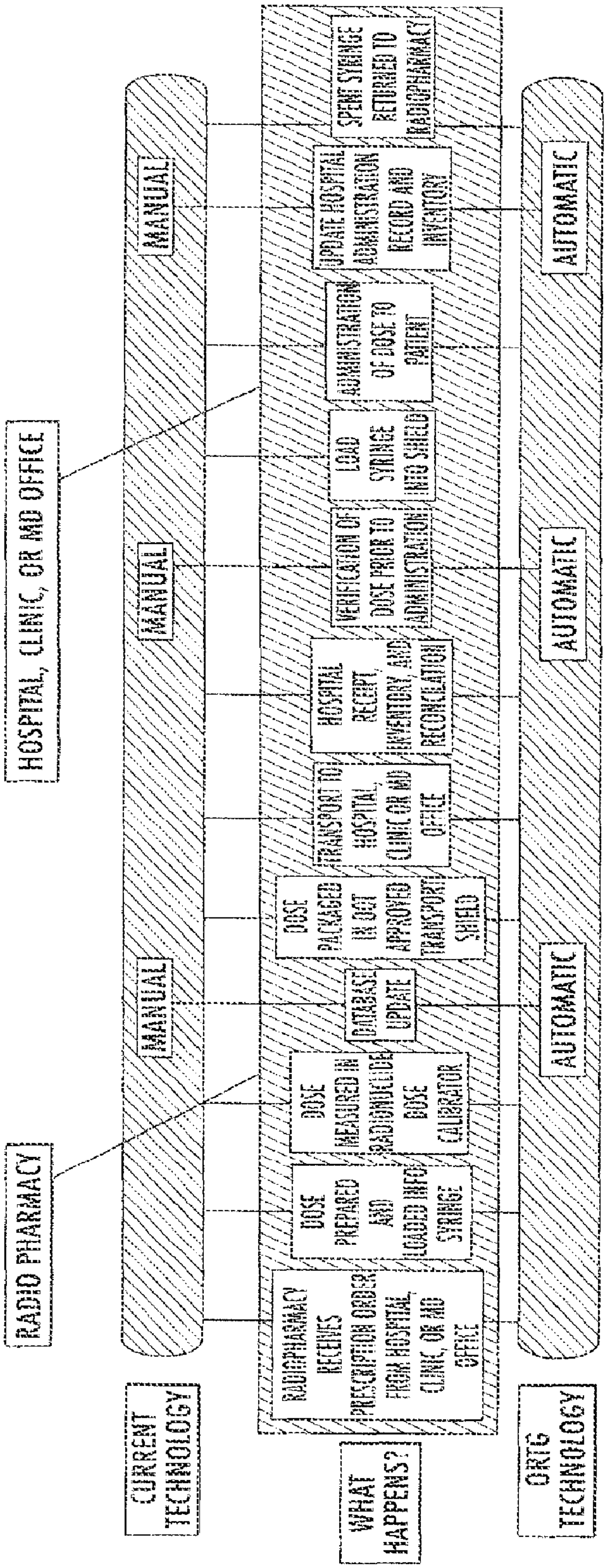
FIG. 23 is a diagram illustrating the flow of a radioactive dose from a pharmacy to a patient and back to the pharmacy and comparing the current invention to current technology.

The SDS is Represented in FIGS. 21-23.

Model A—to safely shield and contain a variety of radionuclides and radiopharmaceuticals including mostly Tc-99m and Tl-201, with gamma energies not greater than approximately 165 keV.

Shielding Design Specifications: Material Construction: Tungsten syringe shield/Lead containment combo Transport Container Shielding to meet appropriate state and/or federal (or other) regulations for transportation The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

Any element in a claim that does not explicitly state "means for" performing a specified function, or "step for" performing a specific function, is not to be interpreted as a "means" or "step" clause as specified in 35 U.S.C.§112, ¶6. In particular, the use of "step of" in the claims herein is not intended to invoke the provisions of 35 U.S.C.§112, ¶6.

What is claimed is:

1. A containment apparatus for use in association with medical treatments that include radioactive substances, the apparatus comprising:

a tubular housing including a first end and a second end, a plurality of bores located proximate the first end of the tubular housing, and a plurality of movable objects located within the plurality of bores;

a cap having a distal end and a proximal end, the proximal end including a receiver, wherein the proximal end is configured for interlocking with the first end of the tubular housing; and a quick release mechanism including a collar movably positioned proximate the first end of the tubular housing, the collar including a first end, a second end, and an engagement surface located proximate the first end of the collar;

wherein the cap may be rapidly attached to the tubular housing by positioning the collar toward the second end of the tubular housing, placing the proximal end of the cap on the first end of the tubular housing, and moving the collar toward the first end of the tubular housing such that the plurality of movable objects are urged into the receiver as the engagement surface engages the plurality of movable objects and the plurality of movable objects engage with the receiver, thereby substantially interlocking the cap with the tubular housing; and wherein the cap may be rapidly removed from the tubular housing by moving the collar toward the second end of the tubular housing so that the engagement surface of the collar no longer urges the plurality of movable objects into the receiver, thereby substantially freeing the cap from the tubular housing.

2. The containment apparatus of claim 1 wherein the quick release mechanism further comprises a biasing member engaged with the collar to bias the collar in a direction toward the first end of the tubular housing.

3. The containment apparatus of claim 1 wherein the plurality of movable members further comprises a plurality of springs engaged with a plurality of pins for biasing the plurality of pins.

4. The containment apparatus of claim 1 wherein the plurality of movable members further comprises a plurality of balls located within the plurality of bores.

5. The containment apparatus of claim 1 further comprising a lower radioactive shield located within the tubular housing and an upper radioactive shield located within the cap.

6. The containment apparatus of claim 1 wherein the engagement surface further comprises an inclined engagement surface.

7. The containment apparatus of claim 1 wherein the receiver further comprises a groove located proximate the proximal end of the cap.

8. The containment apparatus of claim 1 wherein the receiver further comprises a plurality of bores located proximate the proximal end of the cap.

9. The containment apparatus of claim 5 wherein the plurality of movable members further comprises a plurality of springs engaged with a plurality of pins for biasing the plurality of pins.

10. The containment apparatus of claim 5 wherein the plurality of movable members further comprises a plurality of balls located within the plurality of bores.

11. A containment apparatus for use in association with medical treatments that include radioactive substances, the apparatus comprising:

a tubular housing including a first end and a second end;

a cap having a distal end and a proximal end, the proximal end including a receiver, wherein the proximal end is configured for interlocking with and covering the first end of the tubular housing; and a quick release mechanism including a keyed rail including a key, the keyed rail extending from and attached to the proximal end of the cap; wherein the cap further comprises a rail cavity, and wherein the housing further comprises a slotted cavity including a slot along the length of the slotted cavity, and a cutout proximate the open end of the housing, and an opening located along the open end of the housing including a guide bearing located in the opening, wherein the keyed rail is slidably located on the guide bearing along the slotted cavity of the housing, and wherein the key may be mated with the slot in the cavity, thereby allowing the cap to be moved away from the housing while preventing the cap from rotating about the rail.

12. A containment apparatus for use in association with medical treatments that include radioactive substances, the apparatus comprising:

a tubular housing including a first end, a second end, and a plurality of extensions;

a cap having a distal end, a proximal end, and a plurality of substantially planar surfaces; and a quick release mechanism including a flip top arm attached to at least two of the planar surfaces, the flip top arm including a pair of slots, each slot including an angled portion along an end of the slot closest to the cap, wherein at least two of the plurality of extensions are located within the slots, whereby the cap may be rapidly removed along a path defined by the movement of the flip top arm along the extensions.

* * * * *